US012577215B2

(12) United States Patent
Korde et al.

(10) Patent No.: US 12,577,215 B2
(45) Date of Patent: Mar. 17, 2026

(54) TRIAZINE UV ABSORBERS AND A PROCESS FOR THE PREPARATION THEREOF

(71) Applicant: BASF SE, Ludwigshafen (DE)

(72) Inventors: Shilpa Korde, Navi Mumbai (IN); Mushtaq Patel, Navi Mumbai (IN); Amarish Samel, Navi Mumbai (IN); Mudabbir Ansari, Navi Mumbai (IN); Sachin Rane, Navi Mumbai (IN)

(73) Assignee: BASF SE, Ludwigshafen am Rhein (DE)

( * ) Notice: Subject to any disclaimer, the term of this patent is extended or adjusted under 35 U.S.C. 154(b) by 706 days.

(21) Appl. No.: 17/788,683

(22) PCT Filed: Dec. 25, 2020

(86) PCT No.: PCT/EP2020/087893

§ 371 (c)(1),
(2) Date: Jun. 23, 2022

(87) PCT Pub. No.: WO2021/130380

PCT Pub. Date: Jul. 1, 2021

(65) Prior Publication Data

US 2023/0088507 A1 Mar. 23, 2023

(30) Foreign Application Priority Data

Dec. 27, 2019 (EP) .................................... 19219768

(51) Int. Cl.
*C07D 251/24* (2006.01)
*C08K 5/3492* (2006.01)

(52) U.S. Cl.
CPC .......... *C07D 251/24* (2013.01); *C08K 5/3492* (2013.01)

(58) Field of Classification Search
CPC .................................................... C07D 251/24
See application file for complete search history.

(56) References Cited

FOREIGN PATENT DOCUMENTS

| | | | | |
|---|---|---|---|---|
| EP | 0654469 | A1 * | 5/1995 | ........... C07D 251/24 |
| EP | 1310492 | A1 | 5/2003 | |
| JP | 2002518487 | A | 6/2002 | |
| JP | 2012-220567 | A | 11/2012 | |
| JP | 6702493 | B1 | 6/2020 | |
| WO | 99/67225 | A1 | 12/1999 | |
| WO | 2016/097311 | A1 | 6/2016 | |

OTHER PUBLICATIONS

Ngwira et al., European Jnal. of Org. Chem, (2019) pp. 4778-4790.*
Brunetti, et al., "Die Synthese von asymmetrisch substituierten o-Hydroxyphenyl-s-triazinen", Helvetica Chimica Acta, vol. 55, Issue 5, Jul. 10, 1972, pp. 1566-1595.
European Search Report for EP Patent Application No. 19219768.9, Issued on Jun. 29, 2020, 3 pages.
International Search Report for PCT Patent Application No. PCT/EP2020/087893, Issued on Mar. 19, 2021, 4 pages.
Ngwira, et al., "Valorisation of Cashew Nut Shell Liquid Phenolics in the Synthesis of UV Absorbers", European Journal of Organic Chemistry, vol. 2019, Issue 30, Jun. 21, 2019, pp. 4778-4790.

* cited by examiner

*Primary Examiner* — Paul V Ward
(74) *Attorney, Agent, or Firm* — ArentFox Schiff LLP

(57) ABSTRACT

The presently claimed invention relates to novel, highly efficient triazine UV absorbers and a general process for the preparation UV absorber compounds from natural precursors.

23 Claims, No Drawings

TRIAZINE UV ABSORBERS AND A PROCESS FOR THE PREPARATION THEREOF

CROSS-REFERENCE TO RELATED APPLICATIONS

This application is a National Stage Entry of PCT/EP2020/087893, filed Dec. 25, 2020, which claims priority to EP application Ser. No. 19/219,768.9, filed Dec. 27, 2019, the disclosures of each of which are hereby incorporated by reference in their entirety.

FIELD OF THE INVENTION

The presently claimed invention relates to novel, highly efficient triazine UV absorbers and a general process for the preparation UV absorber compounds from natural precursors.

BACKGROUND OF THE INVENTION

Triazine UV absorbers are an important class of organic compounds which have a wide variety of applications. One of the most important areas of application is the protection and stabilization of organic materials such as plastics, polymers, coating materials, and photographic recording materials against damages by light, heat, oxygen, or environmental forces. Other areas of application include cosmetics, fibres, dyes, etc.

Triazine-based UV absorbers typically include at least one 2-oxyaryl substituent on the 1,3,5-triazine ring. Triazine-based UV absorber compounds having aromatic substituents at the 2-, 4-, and 6-positions of the 1,3,5-triazine ring and having at least one of the aromatic rings substituted at the ortho position with a hydroxyl group or blocked hydroxyl group are generally the preferred compounds.

There are several processes known in the literature for the preparation of triazine-based UV absorbers. (See, H. Brunetti and C. E. Luethi, [0008] Helvetica Chimica Acta, 1972, 55, 1566-1595, S. Tanimoto et al., Senryo to Yakahin, 1995, 40(120), 325-339).

Many of the approaches consist of three stages. The first stage involves the synthesis of the key intermediate, 2-chloro-4,6-bisaryl-1,3,5-triazine, from commercially available materials and can include single-step or multi-step processes. Thereafter, in the second stage, 2-chloro-4,6-bisaryl-1,3,5-triazine is subsequently arylated with 1,3-dihydroxybenzene (resorcinol) or a substituted 1,3-dihydroxybenzene in the presence of a Lewis acid to form the parent compound 2-(2,4-dihydroxyaryl)-4,6-bisaryl-1,3,5-triazine. The parent compound 2-(2,4-dihydroxyaryl)-4,6-bisaryl-1,3,5-triazine, as mentioned above, may be further functionalized, e.g., alkylated, to prepare a final product, such as 2-(2-hydroxy-4-alkoxyaryl)-4,6-bisaryl-1,3,5-triazine.

*Eur. J. Org. Chem.* 2019, 4778-4790 discloses xylochemical synthesis of different classes of aromatic UV absorbers utilizing cashew nut shell liquid as a non-edible bio-renewable carbon source. It discloses synthesis of 2-(4,6-diphenyl-1,3,5-triazin-2-yl)phenol and 2, 2',2"-(1,3,5-triazine-2,4,6-triyl)triphenol. 2-(4,6-diphenyl-1,3,5-triazin-2-yl)phenol synthesized by formylating cardanol followed by LAH reduction provided substituted benzyl alcohol. Reacting the alcohol with benzamidine yielded 2-(4,6-diphenyl-1,3,5-triazin-2-yl)phenol. 2, 2',2"-(1,3,5-triazine-2,4,6-triyl)triphenol was synthesized by converting formylated cardanol to nitrile intermediate. The trimerization of the nitrile intermediate using microwave irradiation yield 2, 2',2"-(1,3,5-triazine-2,4,6-triyl)triphenol.

A high number of UV absorbers is commercially available and being used extensively in different technological areas. Still there is a need to develop UV absorbers having better UV absorbance and having lower haziness and coloration in the application. Further, with current concerns over the use of fossil resources for chemical synthesis it is envisaged to utilizate renewable resources for the synthesis of the chemical compounds.

Thus, it is an object of the presently claimed invention to provide highly efficient UV absorbers having low haziness and coloration, while applied in a composition, which can be prepared via a short and widely applicable route from renewable resources as starting material.

SUMMARY OF THE INVENTION

Surprisingly, it was found that triazine compounds having at least one substituted or unsubstituted, linear or branched $C_{12}$-$C_{16}$ alkyl or substituted or unsubstituted, linear or branched $C_{12}$-$C_{16}$ alkenyl on at least one of the phenyl group attached to the triazine group can be prepared via acid catalysis via a short and widely applicable route from easily available renewable resources and show high UV absorbance and low haziness and coloration while applied in a composition.

Accordingly, the main aspect of the presently claimed invention is directed to a process for the preparation of a compound of formula (A), comprising at least the step of:

i. reacting at least one compound of formula (D) selected from the group consisting of formulae (D1), (D2) and (D3), formula (D)

formula (D1)

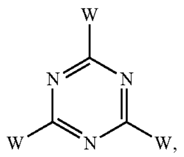

formula (D2)

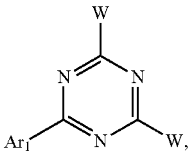

and formula (D3)

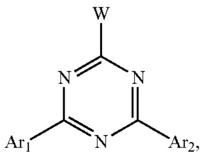

wherein W is selected from the group consisting of F, Cl, and Br; and wherein $Ar_1$ and $Ar_2$ are independently of each other a moiety of the formula (B) or a moiety of the formula (J), formula (B)

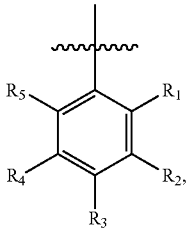

formula (J)

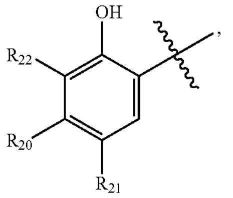

wherein $R_1$, $R_2$, $R_3$, $R_4$ and $R_5$ are independently selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl, substituted or unsubstituted $C_7$-$C_{24}$ arylalkyl, —C(═O)—R, —OR, —NRR', —C(═O)—NRR', —CN, —SR, —S(═O)$_2$R, —S(═O)$_2$OH and —S(═O)$_2$OM; wherein M is an alkali metal; or $R_1$ and $R_2$ together with the carbon atoms to which they are bonded or $R_2$ and $R_3$ together with the carbon atoms to which they are bonded or $R_3$ and $R_4$ together with the carbon atoms to which they are bonded or $R_4$ and $R_5$ together with the carbon atoms to which they are bonded form a saturated or unsaturated, unsubstituted or substituted 5- to 20-membered carbocyclic ring that optionally contains 1, 2 or 3 heteroatom(s) selected from O, N or S as ring member(s);

R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;

with least one compound of formula (E), formula (E)

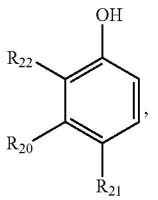

wherein $R_{20}$ is selected from the group consisting of substituted or unsubstituted, linear or branched $C_{12}$-$C_{16}$ alkyl and substituted or unsubstituted, linear or branched $C_{12}$-$C_{16}$ alkenyl;

$R_{21}$ is selected from the group consisting of hydrogen, substituted or unsubstituted, linear or branched $C_{12}$-$C_{16}$ alkyl and substituted or unsubstituted, linear or branched $C_{12}$-$C_{16}$ alkenyl;

$R_{22}$ is selected from the group consisting of hydrogen and substituted or unsubstituted, linear or branched $C_1$-$C_{24}$ alkyl; or $R_{20}$ and $R_{21}$ together with the carbon atoms to which they are bonded form a saturated or unsaturated, unsubstituted or substituted 5- to 20-membered carbocyclic ring that optionally contains 1, 2 or 3 heteroatom(s) selected from O, N or S as ring member(s);

in the presence of at least one acid; and ii. optionally reacting the reaction product of step i. with at least one compound of formula (G), formula (G)

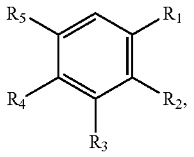

wherein $R_1$, $R_2$, $R_3$, $R_4$ and $R_5$ are defined as above, in the presence of at least one acid.

A second aspect of the presently claimed invention is directed to a compound of formula (A), formula (A)

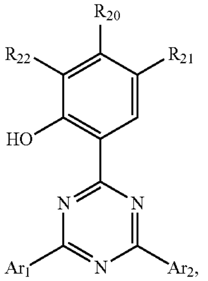

wherein $Ar_1$ and $Ar_2$ are independently of each other a moiety of the formula (B) or a moiety of the formula (J), formula (B)

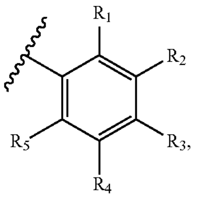

formula (J)

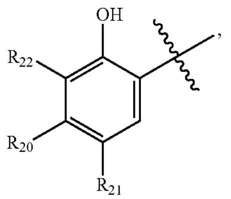

wherein $R_1$, $R_2$, $R_3$, $R_4$ and $R_5$ are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ aryl, substituted or unsubstituted $C_7$-$C_{24}$ arylalkyl, —C(═O)—R, —OR; or $R_1$ and $R_2$ together with the carbon atoms to which they are bonded or $R_2$ and $R_3$ together with the carbon atoms to which they are bonded or $R_3$ and $R_4$ together with the carbon atoms to which they are bonded or $R_4$ and $R_5$ together with the carbon atoms to which they are bonded to form a saturated or unsaturated, unsubstituted or substituted 5- to 20-membered carbocyclic ring that optionally contains 1, 2 or 3 heteroatom(s) selected from O, N or S as ring member(s); and R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;

$R_{20}$ is selected from the group consisting of substituted or unsubstituted, linear or branched $C_{12}$-$C_{16}$ alkyl, substituted or unsubstituted and linear or branched $C_{12}$-$C_{16}$ alkenyl; and $R_{21}$ is selected from the group consisting of hydrogen, substituted or unsubstituted, linear or branched $C_{12}$-$C_{16}$ alkyl and substituted or unsubstituted, linear or branched $C_{12}$-$C_{16}$ alkenyl;

$R_{22}$ is selected from the group consisting of hydrogen and substituted or unsubstituted, linear or branched $C_1$-$C_6$ alkyl; or $R_{20}$ and $R_{21}$ together with the carbon atoms to which they are bonded form a saturated or unsaturated, 5- to 20-membered carbocyclic ring that is unsubstituted or substituted with 1, 2 or 3 substituents selected from the group consisting of halogen, substituted or unsubstituted, linear or branched $C_1$-$C_{24}$ alkyl, substituted or unsubstituted, linear or branched $C_2$-$C_{24}$ alkenyl and substituted or unsubstituted $C_6$-$C_{24}$ aryl, and that optionally contains 1, 2 or 3 heteroatom(s) selected from O, N or S as ring member(s);

wherein the following compounds of formula (A) are excluded: 2-[4,6-bis(2-hydroxy-4-pentadecyl-phenyl)-1,3,5-triazin-2-yl]-5-pentadecyl-phenol and 2-(4,6-diphenyl-1,3,5-triazin-2-yl)-5-pentadecylphenol.

DETAILED DESCRIPTION

Before the present compositions and formulations of the presently claimed invention are described, it is to be understood that this invention is not limited to particular compositions and formulations described, since such compositions and formulation may, of course, vary. It is also to be understood that the terminology used herein is not intended to be limiting, since the scope of the presently claimed invention will be limited only by the appended claims.

If hereinafter a group is defined to comprise at least a certain number of embodiments, this is meant to also encompass a group which preferably consists of these embodiments only. Furthermore, the terms 'first', 'second', 'third' or 'a', 'b', 'c', etc. and the like in the description and in the claims, are used for distinguishing between similar elements and not necessarily for describing a sequential or chronological order. It is to be understood that the terms so used are interchangeable under appropriate circumstances and that the embodiments of the presently claimed invention described herein are capable of operation in other sequences than described or illustrated herein. In case the terms 'first', 'second', 'third' or '(A)', '(B)' and '(C)' or '(a)', '(b)', '(c)', '(d)', 'i', 'ii' etc. relate to steps of a method or use or assay there is no time or time interval coherence between the steps, that is, the steps may be carried out simultaneously or there may be time intervals of seconds, minutes, hours, days, weeks, months or even years between such steps, unless otherwise indicated in the application as set forth herein above or below.

Furthermore, the ranges defined throughout the specification include the end values as well i.e. a range of 1 to 10 implies that both 1 and 10 are included in the range. For the avoidance of doubt, applicant shall be entitled to any equivalents according to applicable law.

In the following passages, different aspects of the presently claimed invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to 'one embodiment' or 'an embodiment' means that a particular feature, structure or characteristic described in connection with the embodiment is included in at least one embodiment of the presently claimed invention. Thus, appearances of the phrases 'in one embodiment' or 'in an embodiment' in various places throughout this specification are not necessarily all referring to the same embodiment, but may.

Furthermore, the particular features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the presently claimed invention, and form different embodiments, as would be understood by those in the art. For example, in the appended claims, any of the claimed embodiments can be used in any combination.

In an embodiment, the presently claimed invention is directed to a process for the preparation of a compound of formula (A1), formula (A1)

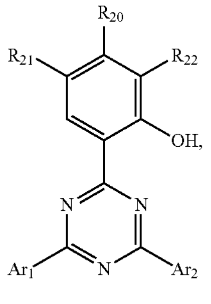

wherein $Ar_1$ and $Ar_2$ are independently of each other a moiety of the formula (B) or a moiety of the formula (J), formula (B)

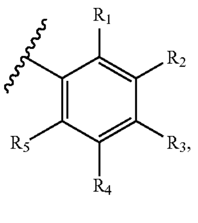

-continued formula (J)

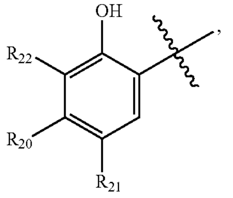

wherein in each formulae $R_1$, $R_2$, $R_3$, $R_4$, $R_5$, $R_{20}$, $R_{21}$ and $R_{22}$ are defined as below, comprising at least the step of:

i. reacting at least one compound of formula (D) selected from the group consisting of formulae (D1), (D2) and (D3), formula (D)

formula (D1)

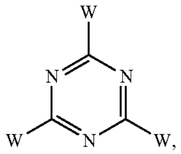

formula (D2)

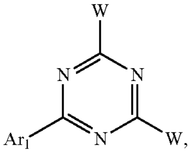

and formula (D3)

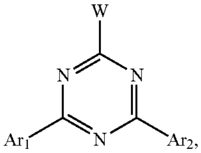

wherein W is selected from the group consisting of F, Cl, and Br; and wherein $Ar_1$ and $Ar_2$ are independently of each other a moiety of the formula (B) or a moiety of the formula (J), formula (B)

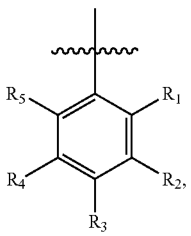

formula (J)

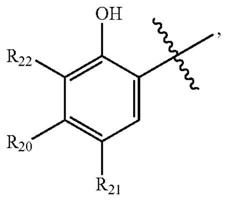

wherein $R_1$, $R_2$, $R_3$, $R_4$ and $R_5$ are independently selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl, substituted or unsubstituted $C_7$-$C_{24}$ arylalkyl, —C(═O)—R, —OR, —NRR', —C(═O)—NRR', —CN, —SR, —S(═O)$_2$R, —S(═O)$_2$OH and —S(═O)$_2$OM; wherein M is an alkali metal; or $R_1$ and $R_2$ together with the carbon atoms to which they are bonded or $R_2$ and $R_3$ together with the carbon atoms to which they are bonded or $R_3$ and $R_4$ together with the carbon atoms to which they are bonded or $R_4$ and $R_5$ together with the carbon atoms to which they are bonded form a saturated or unsaturated, unsubstituted or substituted 5- to 20-membered carbocyclic ring that optionally contains 1, 2 or 3 heteroatom(s) selected from O, N or S as ring member(s);

R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;

$R_{20}$ is selected from the group consisting of substituted or unsubstituted, linear or branched $C_{12}$-$C_{16}$ alkyl and substituted or unsubstituted, linear or branched $C_{12}$-$C_{16}$ alkenyl;

$R_{21}$ is selected from the group consisting of hydrogen, substituted or unsubstituted, linear or branched $C_{12}$-$C_{16}$ alkyl and substituted or unsubstituted, linear or branched $C_{12}$-$C_{16}$ alkenyl;

$R_{22}$ is selected from the group consisting of hydrogen and substituted or unsubstituted, linear or branched $C_1$-$C_{24}$ alkyl; or $R_{20}$ and $R_{21}$ together with the carbon atoms to which they are bonded form a saturated or unsaturated, unsubstituted or substituted 5- to 20-membered carbocyclic ring that optionally contains 1, 2 or 3 heteroatom(s) selected from O, N or S as ring member(s);

with least one compound of formula (E), formula (E)

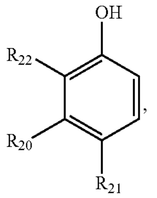

wherein $R_{20}$, $R_{21}$ and $R_{22}$ are defined as above, in the presence of at least one acid; and ii. optionally reacting the reaction product of step i. with at least one compound of formula (G), formula (G)

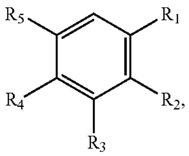

wherein $R_1$, $R_2$, $R_3$, $R_4$ and $R_5$ are defined as above, in the presence of at least one acid;

more preferably the presently claimed invention is directed to a process for the preparation of a compound of formula (A1), formula (A1)

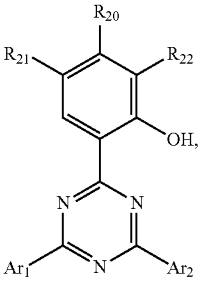

wherein $Ar_1$ and $Ar_2$ are independently of each other a moiety of the formula (B) or a moiety of the formula (J), formula (B)

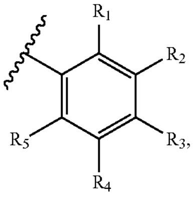

formula (J)

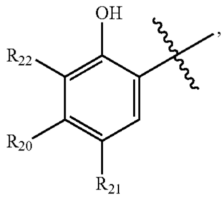

, wherein in each formulae $R_1$, $R_2$, $R_3$, $R_4$, $R_5$, $R_{20}$, $R_{21}$ and $R_{22}$ are defined as below, comprising at least the step of:

i. reacting at least one compound of formula (D) selected from the group consisting of formulae (D1), (D2) and (D3), formula (D)

formula (D1)

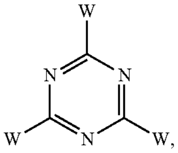

formula (D2)

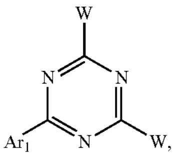

and

-continued formula (D3)

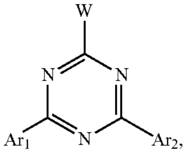

wherein W is Cl; and wherein $Ar_1$ and $Ar_2$ are independently of each other a moiety of the formula (B) or a moiety of the formula (J), formula (B)

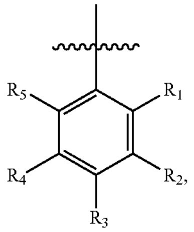

formula (J)

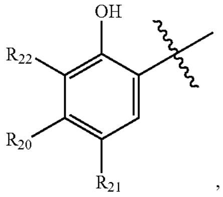

, wherein $R_1$, $R_2$, $R_3$, $R_4$ and $R_5$ are independently selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, —C(=O)—R, —OR, —NRR', —C(=O)—NRR', —CN, —SR, —S(=O)$_2$R, —S(=O)$_2$OH and —S(=O)$_2$OM; wherein M is an alkali metal; or $R_1$ and $R_2$ together with the carbon atoms to which they are bonded or $R_2$ and $R_3$ together with the carbon atoms to which they are bonded or $R_3$ and $R_4$ together with the carbon atoms to which they are bonded or $R_4$ and $R_5$ together with the carbon atoms to which they are bonded form a saturated or unsaturated, unsubstituted or substituted 5- to 20-membered carbocyclic ring that optionally contains 1, 2 or 3 heteroatom(s) selected from O, N or S as ring member(s);

R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl and substituted or unsubstituted $C_7$-$C_{24}$ arylalkyl;

$R_{20}$ is selected from the group consisting of substituted or unsubstituted, linear or branched $C_{12}$-$C_{16}$ alkyl and substituted or unsubstituted, linear or branched $C_{12}$-$C_{16}$ alkenyl;

$R_{21}$ is selected from the group consisting of hydrogen, substituted or unsubstituted, linear or branched $C_{12}$-$C_{16}$ alkyl and substituted or unsubstituted, linear or branched $C_{12}$-$C_{16}$ alkenyl;

$R_{22}$ is selected from the group consisting of hydrogen and substituted or unsubstituted, linear or branched $C_1$-$C_{24}$ alkyl; or $R_{20}$ and $R_{21}$ together with the carbon atoms to which they are bonded form a saturated or unsaturated, unsubstituted or substituted 5- to 20-membered carbocyclic ring that optionally contains 1, 2 or 3 heteroatom(s) selected from O, N or S as ring member(s);

with least one compound of formula (E), formula (E)

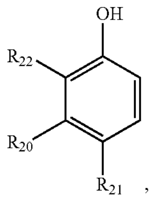
, wherein $R_{20}$, $R_{21}$ and $R_{22}$ are defined as above, in the presence of at least one acid; and ii. optionally reacting the reaction product of step i. with at least one compound of formula (G), formula (G)

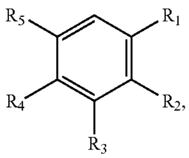

wherein $R_1$, $R_2$, $R_3$, $R_4$ and $R_5$ are defined as above, in the presence of at least one acid;

even more preferably the presently claimed invention is directed to a process for the preparation of a compound of formula (A1), formula (A1)

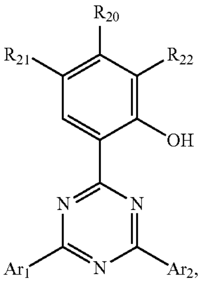

wherein $Ar_1$ and $Ar_2$ are independently of each other a moiety of the formula (B) or a moiety of the formula (J), formula (B)

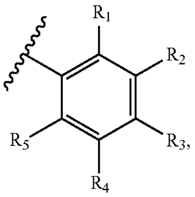

-continued formula (J)

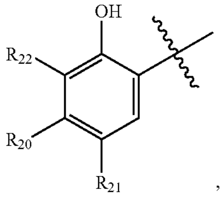
, wherein in each formulae $R_1$, $R_2$, $R_3$, $R_4$, $R_5$, $R_{20}$, $R_{21}$ and $R_{22}$ are defined as below, comprising at least the step of:

i. reacting at least one compound of formula (D) selected from the group consisting of formulae (D1), (D2) and (D3), formula (D)

formula (D1)

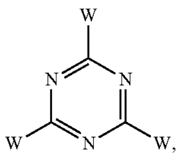

formula (D2)

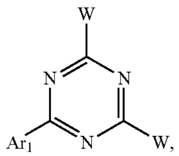
and formula (D3)

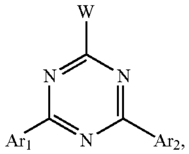

wherein W is Cl; and wherein $Ar_1$ and $Ar_2$ are independently of each other a moiety of the formula (B) or a moiety of the formula (J), formula (B)

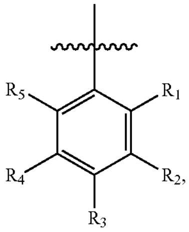

formula (J)

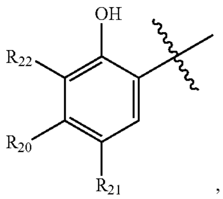
, wherein $R_1$, $R_2$, $R_3$, $R_4$ and $R_5$ are independently selected from the group consisting of hydrogen, halogen, substituted or unsubstituted, linear or branched $C_1$-$C_{24}$ alkyl, substituted or unsubstituted $C_6$-$C_{24}$ aryl, substituted or unsubstituted $C_7$-$C_{24}$ arylalkyl, —C(═O)—R, —OR, —NRR', —C(═O)—NRR', —CN, —SR, —S(═O)$_2$R, —S(═O)$_2$OH and —S(═O)$_2$OM; wherein M is an alkali metal;

R and R' are independently selected from the group consisting of hydrogen, substituted or unsubstituted, linear or branched $C_1$-$C_{24}$ alkyl, substituted or unsubstituted $C_6$-$C_{24}$ aryl and substituted or unsubstituted $C_7$-$C_{24}$ arylalkyl;

$R_{20}$ is selected from the group consisting of substituted or unsubstituted, linear or branched $C_{12}$-$C_{16}$ alkyl;

$R_{21}$ is selected from the group consisting of hydrogen, substituted or unsubstituted, linear or branched $C_{12}$-$C_{16}$ alkyl;

$R_{22}$ is selected from the group consisting of hydrogen and substituted or unsubstituted, linear or branched $C_1$-$C_{24}$ alkyl; or $R_{20}$ and $R_{21}$ together with the carbon atoms to which they are bonded form a saturated or unsaturated, unsubstituted or substituted 5- to 20-membered carbocyclic ring that optionally contains 1, 2 or 3 heteroatom(s) selected from O, N or S as ring member(s);

with least one compound of formula (E), formula (E)

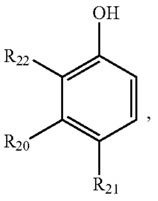

wherein $R_{20}$, $R_{21}$ and $R_{22}$ are defined as above, in the presence of at least one acid; and ii. optionally reacting the reaction product of step i. with at least one compound of formula (G), formula (G)

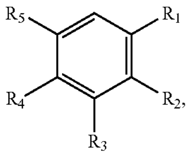

wherein $R_1$, $R_2$, $R_3$, $R_4$ and $R_5$ are defined as above, in the presence of at least one acid;

most preferably the presently claimed invention is directed to a process for the preparation of a compound of formula (A1), formula (A1)

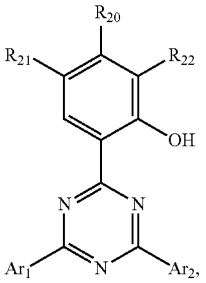

wherein $Ar_1$ and $Ar_2$ are independently of each other a moiety of the formula (B) or a moiety of the formula (J), formula (B)

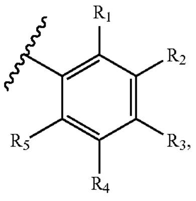

formula (J)

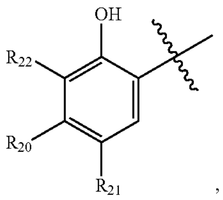

wherein in each formulae $R_1$, $R_2$, $R_3$, $R_4$, $R_5$, $R_{20}$, $R_{21}$ and $R_{22}$ are defined as below, comprising at least the step of:

i. reacting at least one compound of formula (D) selected from the group consisting of formulae (D1), (D2) and (D3), formula (D)

formula (D1)

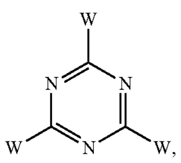

formula (D2)

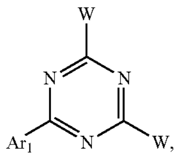

and

-continued formula (D3)

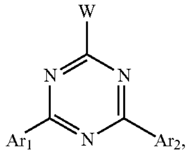

wherein W is Cl; and wherein $Ar_1$ and $Ar_2$ are independently of each other a moiety of the formula (B) or a moiety of the formula (J), formula (B)

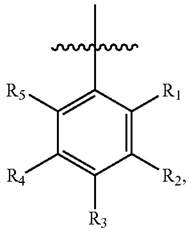

formula (J)

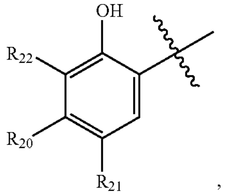

wherein $R_1$, $R_2$, $R_3$, $R_4$ and $R_5$ are independently selected from the group consisting of hydrogen, halogen, substituted or unsubstituted, linear or branched $C_1$-$C_{24}$ alkyl, substituted or unsubstituted $C_6$-$C_{24}$ aryl, substituted or unsubstituted $C_7$-$C_{24}$ arylalkyl, —C(═O)—R, —OR;

R and R' are independently selected from the group consisting of hydrogen, substituted or unsubstituted, linear or branched $C_1$-$C_{24}$ alkyl, substituted or unsubstituted $C_6$-$C_{24}$ aryl and substituted or unsubstituted $C_7$-$C_{24}$ arylalkyl;

$R_{20}$ is selected from the group consisting of substituted or unsubstituted, linear or branched $C_{12}$-$C_{16}$ alkyl;

$R_{21}$ is selected from the group consisting of hydrogen, substituted or unsubstituted, linear or branched $C_{12}$-$C_{16}$ alkyl;

$R_{22}$ is selected from the group consisting of hydrogen and substituted or unsubstituted, linear or branched $C_1$-$C_{24}$ alkyl; or $R_{20}$ and $R_{21}$ together with the carbon atoms to which they are bonded form a saturated or unsaturated, unsubstituted or substituted 5- to 20-membered carbocyclic ring that optionally contains 1, 2 or 3 heteroatom(s) selected from O, N or S as ring member(s);

with least one compound of formula (E), formula (E)

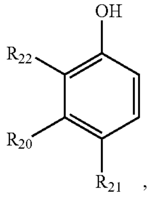

wherein $R_{20}$, $R_{21}$ and $R_{22}$ are defined as above, in the presence of at least one acid; and ii. optionally reacting the reaction product of step i. with at least one compound of formula (G), formula (G)

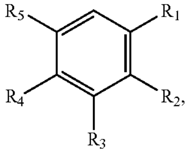

wherein $R_1$, $R_2$, $R_3$, $R_4$ and $R_5$ are defined as above, in the presence of at least one acid;

and in particular the presently claimed invention is directed to a process for the preparation of a compound of formula (A1), formula (A1)

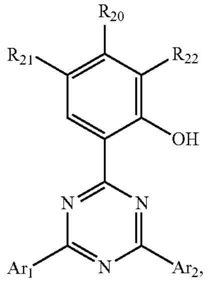

wherein $Ar_1$ and $Ar_2$ are independently of each other a moiety of the formula (B) or a moiety of the formula (J), formula (B)

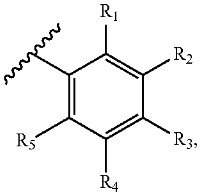

formula (J)

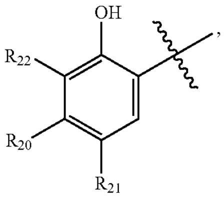

wherein in each formulae $R_1$, $R_2$, $R_3$, $R_4$, $R_5$, $R_{20}$, $R_{21}$ and $R_{22}$ are defined as below, comprising at least the step of:

i. reacting at least one compound of formula (D) selected from the group consisting of formulae (D1), (D2) and (D3), formula (D)

formula (D1)

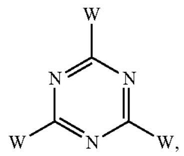

formula (D2)

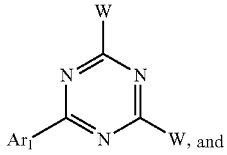

and formula (D3)

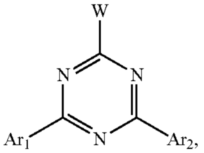

wherein W is Cl; and wherein $Ar_1$ and $Ar_2$ are independently of each other a moiety of the formula (B) or a moiety of the formula (J), formula (B)

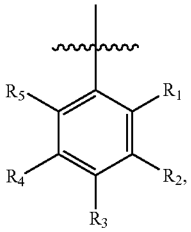

formula (J)

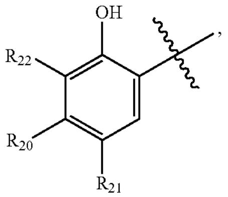

wherein $R_1$, $R_2$, $R_3$, $R_4$ and $R_5$ are independently selected from the group consisting of hydrogen, halogen, substituted or unsubstituted, linear or branched $C_1$-$C_{16}$ alkyl, substituted or unsubstituted $C_6$-$C_{24}$ aryl, —C(=O)—R and —OR;

R and R' are independently selected from the group consisting of hydrogen, substituted or unsubstituted, linear or branched $C_1$-$C_{16}$ alkyl and substituted or unsubstituted $C_6$-$C_{24}$ aryl;

$R_{20}$ is selected from the group consisting of substituted or unsubstituted, linear or branched $C_{14}$-$C_{16}$ alkyl;

$R_{21}$ is selected from the group consisting of hydrogen, substituted or unsubstituted, linear or branched $C_{14}$-$C_{16}$ alkyl;

$R_{22}$ is selected from the group consisting of hydrogen and substituted or unsubstituted, linear or branched $C_1$-$C_{16}$ alkyl; or $R_{20}$ and $R_{21}$ together with the carbon atoms to which they are bonded form a saturated or unsaturated, unsubstituted or substituted 5- to 10-membered carbocyclic ring that optionally contains 1, 2 or 3 heteroatom(s) selected from O, N or S as ring member(s);

with least one compound of formula (E), formula (E)

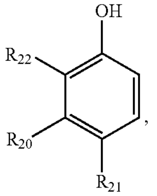

wherein $R_{20}$, $R_{21}$ and $R_{22}$ are defined as above, in the presence of at least one Lewis acid; and ii. optionally reacting the reaction product of step i. with at least one compound of formula (G), formula (G)

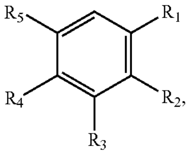

wherein $R_1$, $R_2$, $R_3$, $R_4$ and $R_5$ are defined as above, in the presence of at least one Lewis acid.

In another preferred embodiment, $R_1$, $R_2$, $R_3$, $R_4$ and $R_5$ are independently selected from the group consisting of hydrogen, halogen, substituted or unsubstituted, linear or branched $C_1$-$C_{24}$ alkyl, substituted or unsubstituted $C_6$-$C_{24}$ aryl, —C(=O)—R and —OR, wherein R is selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl.

In another preferred embodiment, $R_1$ is selected from the group consisting of hydrogen, halogen, substituted or unsubstituted, linear or branched $C_1$-$C_{24}$ alkyl, substituted or unsubstituted $C_6$-$C_{24}$ aryl, —C(=O)—R and —OR;

$R_2$ is selected from the group consisting of hydrogen, halogen, substituted or unsubstituted, linear or branched $C_1$-$C_{24}$ alkyl, substituted or unsubstituted $C_6$-$C_{24}$ aryl, substituted or unsubstituted $C_7$-$C_{24}$ arylalkyl, —C(=O)—R, —OR, —C(=O)—NRR', —CN, —S(=O)$_2$OH and —S(=O)$_2$OM; wherein M is an alkali metal;

$R_3$ is selected from the group consisting of hydrogen, halogen, substituted or unsubstituted, linear or branched $C_1$-$C_{24}$ alkyl, substituted or unsubstituted $C_6$-$C_{24}$ aryl, substituted or unsubstituted $C_7$-$C_{24}$ arylalkyl, —C(=O)R, —OR, —C(=O)—NRR', —S(=O)$_2$OH and —S(=O)$_2$ OM; wherein M is an alkali metal;

$R_4$ is selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, —C(═O)R, —OR, —NRR', —C(═O)—NRR', —S(═O)$_2$OH and —S(═O)$_2$OM; wherein M is an alkali metal; and $R_5$ is selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, —C(═O)R, —OR, —NRR', —C(═O)—NRR', —S(═O)$_2$OH and —S(═O)$_2$OM; wherein M is an alkali metal;

R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;

wherein, in case of substitution, $C_1$-$C_{24}$ alkyl and $C_2$-$C_{24}$ alkenyl are substituted with 1, 2 or 3 substituents selected from the group consisting of —O—, OH, CN, $NH_2$, —N($C_1$-$C_5$ alkyl)$_2$, —N($C_1$-$C_5$-alkyl)(phenyl), —N($C_1$-$C_5$ alkyl)($CH_2$phenyl), —N($C_1$-$C_5$-alkyl)($CH_2$—$CH_2$-phenyl), —O—$CF_3$, —SH, —C(═O)—H, —C(═O)—$C_1$-$C_5$-alkyl, —C(═O)-phenyl, —C(═O)—OH, —C(═O)—O—($C_1$-$C_{20}$-alkyl), —C(═O)—O—($C_1$-$C_{20}$-alkyl), —C(═O)—O-phenyl, —O—C(═O)—($C_1$-$C_{20}$-alkyl), —O—C(═O)—($C_1$-$C_{20}$-alkenyl), —O—C(═O)-(phenyl), —C(═O)—$NH_2$, —C(═O)—NH—($C_1$-$C_5$-alkyl), —C(═O)—N($C_1$-$C_5$-alkyl)$_2$, and unsubstituted $C_6$-$C_{24}$ aryl;

$C_5$-$C_{24}$ cycloalkyl and $C_5$-$C_{24}$ cycloalkenyl are substituted with 1, 2 or 3 substituents selected from the group consisting of unsubstituted, linear or branched $C_1$-$C_{24}$ alkyl, unsubstituted, linear or branched $C_2$-$C_{24}$ alkenyl, CN, $NH_2$, —N($C_1$-$C_5$ alkyl)$_2$, —N($C_1$-$C_5$-alkyl)(phenyl), —N($C_1$-$C_5$ alkyl)($CH_2$phenyl), —N($C_1$-$C_5$-alkyl)($CH_2$—$CH_2$-phenyl), —O—$CF_3$, —SH, —C(═O)—H, —C(═O)—$C_1$-$C_5$-alkyl, —C(═O)-phenyl, —C(═O)—OH, —C(═O)—O—($C_1$-$C_5$-alkyl), —C(═O)—O-phenyl, —C(═O)—$NH_2$, —C(═O)—NH—($C_1$-$C_5$-alkyl), —C(═O)—N($C_1$-$C_5$-alkyl)$_2$, and unsubstituted $C_6$-$C_{24}$ aryl and unsubstituted $C_6$-$C_{24}$ aryl;

$C_6$-$C_{24}$ aryl and $C_7$-$C_{24}$ arylalkyl are substituted with 1, 2 or 3 substituents selected from the group consisting of halogens, —CN, —S(═O)$_2$OH, —OH, —O($C_1$-$C_5$ alkyl), —O(phenyl), O($CH_2$phenyl), —O($CH_2$—$CH_2$-phenyl), S—(═O)$_2$OM, $CH_3$, $C_2H_5$, $C_3H_7$, $C_8H_{17}$, $C_{15}H_{31}$, $NH_2$, —O—$CF_3$, —SH, —N($C_1$-$C_5$ alkyl)$_2$, —N($C_1$-$C_5$-alkyl)(phenyl), —N($C_1$-$C_5$ alkyl)($CH_2$phenyl), —N($C_1$-$C_5$-alkyl)($CH_2$—$CH_2$-phenyl), —C(═O)—H, —C(═O)—$C_1$-$C_5$-alkyl, —C(═O)-phenyl, —C(═O)—OH, —C(═O)—O—($C_1$-$C_5$-alkyl), —C(═O)—O-phenyl, —C(═O)—$NH_2$, —C(═O)—NH—($C_1$-$C_5$-alkyl), —C(═O)—N($C_1$-$C_5$-alkyl)$_2$, and unsubstituted $C_6$-$C_{24}$ aryl;

more preferably $R_1$ is selected from the group consisting of hydrogen substituted or unsubstituted, linear or branched $C_1$-$C_{24}$ alkyl and OR;

$R_2$ is selected from the group consisting of hydrogen, substituted or unsubstituted, linear or branched $C_1$-$C_{24}$ alkyl and OR;

$R_3$ is selected from the group consisting of hydrogen, substituted or unsubstituted, linear or branched $C_1$-$C_{24}$ alkyl, substituted or unsubstituted $C_6$-$C_{24}$ aryl, and OR;

$R_4$ is hydrogen; and $R_5$ is hydrogen;

R is selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, and substituted or unsubstituted $C_6$-$C_{24}$ aryl;

wherein, in case of substitution, $C_1$-$C_{24}$ alkyl and $C_2$-$C_{24}$ alkenyl are substituted with 1, 2 or 3 substituents selected from the group consisting of —O—, OH, —C(═O)—$C_1$-$C_{20}$-alkyl, —C(═O)phenyl, —C(═O)—OH, —O—C(═O)—($C_1$-$C_{20}$-alkyl), —O—C(═O)—($C_1$-$C_{20}$-alkenyl), —O—C(═O)-(phenyl), and unsubstituted $C_6$-$C_{24}$ aryl;

$C_6$-$C_{24}$ aryl is substituted with 1, 2 or 3 substituents selected from the group consisting of OH, O($C_1$-$C_{24}$ alkyl), O(phenyl), O($CH_2$phenyl), O($CH_2$—$CH_2$-phenyl), $CH_3$, $C_2H$, $C_3H_7$, $C_8H_{17}$, $C_{15}H_{31}$, —C(═O)—$C_1$-$C_{24}$-alkyl, —C(═O)-phenyl, —C(═O)—O—($C_1$-$C_5$-alkyl), —C(═O)—O-phenyl, and unsubstituted $C_6$-$C_{24}$ aryl.

In another preferred embodiment, $R_{20}$ is selected from the group consisting of linear or branched $C_{12}$-$C_{16}$ alkyl and linear or branched $C_{12}$-$C_{16}$ alkenyl; which are in each case unsubstituted or substituted with 1, 2 or 3 substituents selected from the group consisting of —OR, —S(═O)$_2$OH, —S(═O)$_2$OM, and —O—C(═O)—R, wherein M is an alkali metal;

R is selected from the group consisting of hydrogen, unsubstituted, linear or branched $C_1$-$C_{24}$ alkyl, unsubstituted, linear or branched $C_2$-$C_{24}$ alkenyl, unsubstituted $C_5$-$C_{24}$ cycloalkyl, unsubstituted $C_5$-$C_{24}$ cycloalkenyl, unsubstituted $C_6$-$C_{24}$ aryl and unsubstituted $C_7$-$C_{24}$ arylalkyl;

$R_{21}$ is selected from the group consisting of hydrogen, linear or branched $C_{12}$-$C_{16}$ alkyl and linear or branched $C_{12}$-$C_{16}$ alkenyl; which are in each case unsubstituted or substituted with 1, 2 or 3 substituents selected from the group consisting of —OR, —S(═O)$_2$OH, —S(═O)$_2$OM, and —O—C(═O)—R, moieties of formula (c1) and moieties of formula (c2), formula (c1)

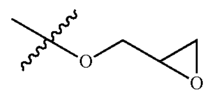

formula (c2)

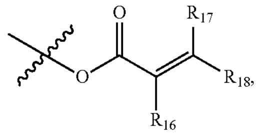

wherein M is an alkali metal;

R, $R_{16}$, $R_{17}$ and $R_{18}$ are independently selected from the group consisting of hydrogen, unsubstituted, linear or branched $C_1$-$C_{24}$ alkyl, unsubstituted, linear or branched $C_2$-$C_{24}$ alkenyl, unsubstituted $C_5$-$C_{24}$ cycloalkyl, unsubstituted $C_5$-$C_{24}$ cycloalkenyl, unsubstituted $C_6$-$C_{24}$ aryl and unsubstituted $C_7$-$C_{24}$ arylalkyl; or $R_{20}$ and $R_{21}$ together with the carbon atoms to which they are bonded form a saturated or unsaturated, 5- to 20-membered carbocyclic ring that is unsubstituted or substituted with 1, 2 or 3 substituents selected from the group consisting of halogen, unsubstituted, linear or branched $C_1$-$C_{24}$ alkyl, unsubstituted, linear or branched $C_2$-$C_{24}$ alkenyl and unsubstituted $C_6$-$C_{24}$ aryl, and that optionally contains 1, 2 or 3 heteroatom(s) selected from O, N or S as ring member(s).

In another preferred embodiment, $R_{20}$ is selected from the group consisting of linear or branched $C_{14}$-$C_{16}$ alkyl and linear or branched $C_{14}$-$C_{16}$ alkenyl; which are in each case unsubstituted or substituted with 1, 2 or 3 substituents selected from the group consisting of —OR, —S—(═O)$_2$ OH, —S(═O)$_2$OM, and —O—C(═O)—R, moieties of formula (c1) and moieties of formula (c2), formula (c1)

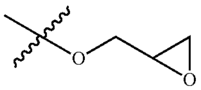

formula (c2)

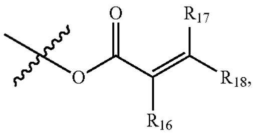

wherein M is an alkali metal;

R, $R_{16}$, $R_{17}$ and $R_{18}$ are as defined as above; or $R_{20}$ and $R_{21}$ together with the carbon atoms to which they are bonded form a saturated or unsaturated, 5- to 20-membered carbocyclic ring.

Within the context of the presently claimed invention, the term "alkyl", as used herein, refers to an acrylic saturated aliphatic group, including linear or branched alkyl saturated hydrocarbon radicals, denoted by a general formula $C_nH_{2n+1}$ and wherein n is the number of carbon atoms such as 1, 2, 3, 4, etc.

In a preferred embodiment, the unsubstituted linear $C_1$-$C_{24}$ alkyl is preferably selected from the group consisting of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, henicosyl, docosyl, tricosyl and tetracosyl; more preferably selected from the group consisting of hexyl, heptyl, octyl, nonyl, decyl, undecyl, dodecyl, tridecyl, tetradecyl, pentadecyl, hexadecyl, heptadecyl, octadecyl, nonadecyl, eicosyl, henicosyl, docosyl, tricosyl and tetracosyl; even more preferably selected from the group consisting of methyl, ethyl, propyl, butyl, pentyl, hexyl, heptyl, octyl, nonyl, decyl, undecyl, dodecyl, tridecyl, tetradecyl and pentadecyl; most preferably selected from the group consisting of methyl, ethyl, propyl, butyl, pentyl, hexyl, heptyl, octyl, nonyl, decyl, undecyl and dodecyl; and in particular selected from the group consisting of methyl, ethyl, propyl, butyl, pentyl, hexyl, heptyl, octyl, nonyl and decyl.

In a preferred embodiment, the unsubstituted branched $C_1$-$C_{24}$ alkyl is preferably selected from the group consisting of isopropyl, iso-butyl, neo-pentyl, 2-ethyl-hexyl, 2-propyl-heptyl, 2-butyl-octyl, 2-pentyl-nonyl, 2-hexyl-decyl, iso-hexyl, iso-heptyl, iso-octyl, iso-nonyl, isodecyl, iso-dodecyl, iso-tetradecyl, iso-hexadecyl, iso-octadecyl and iso-eicosyl, more preferably selected from the group consisting of 2-ethyl-hexyl, 2-propyl-heptyl, 2-butyl-octyl, 2-pentyl-nonyl, 2-hexyl-decyl, iso-hexyl, iso-heptyl, iso-octyl, iso-nonyl, iso-decyl, iso-dodecyl, iso-tetradecyl, iso-hexadecyl, iso-octadecyl, iso-eicosyl, 2-methyltricosyl, 2-ethyldocosyl, 3-ethylhenicosyl, 3-ethylicosyl, 4-propylhenicosyl, propylnonadecyl, 6-butyldodecyl and 5-ethylundecyl.

In a preferred embodiment, the substituted, linear or branched $C_1$-$C_{24}$ alkyl refers to a branched or linear saturated hydrocarbon group having $C_1$-$C_{24}$carbon atoms substituted with functional groups selected from the group consisting of hydroxy, alkoxy, C(═O)—R, CN, C(═O)OR, C(═O)—$NR_2$, $NR_2$ and SR, wherein R is selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl.

In a preferred embodiment, the substituted, linear or branched $C_1$-$C_{24}$ alkyl refers to a branched or linear saturated hydrocarbon group having $C_1$-$C_{24}$carbon atoms substituted with functional groups selected from the group consisting of hydroxy, alkoxy, C(═O)—R, CN, C(═O)OR, C(═O)—$NR_2$, $NR_2$ and SR, preferably selected from the group consisting of 1-hydroxy methyl, 1-methoxy methyl, 1-hydroxy ethyl, 1-hydroxy propyl, 1-hydroxy butyl, 1-hydroxy pentyl, 1-hydroxy hexyl, 1-hydroxy heptyl, 1-hydroxy octyl, 1-hydroxy nonyl, decyl, 1-hydroxy undecyl, 1-hydroxy dodecyl, 1-hydroxy tridecyl, 1-hydroxy tetradecyl, 1-hydroxy pentadecyl, 1-hydroxy hexadecyl, 1-hydroxy heptadecyl, 1-hydroxy octadecyl, 1-hydroxy nonadecyl, 1-hydroxy eicosyl, 1-hydroxy henicosyl, 1-hydroxy docosyl, 1-hydroxy tricosyl, 1-hydroxy tetracosyl, 1-methoxy methyl, 1-methoxy ethyl, 1-methoxy propyl, 1-methoxy butyl, 1-methoxy pentyl, 1-methoxy hexyl, 1-methoxy heptyl, 1-methoxy octyl, 1-methoxy nonyl, decyl, 1-methoxy undecyl, 1-methoxy dodecyl, 1-methoxy tridecyl, 1-methoxy tetradecyl, 1-methoxy pentadecyl, 1-methoxy hexadecyl, 1-methoxy heptadecyl, 1-methoxy octadecyl, 1-methoxy nonadecyl, 1-methoxy eicosyl, 1-methoxy henicosyl, 1-methoxy docosyl, 1-methoxy tricosyl, 1-methoxy tetracosyl, 2-methoxy propyl, 2-methoxy butyl, 2-methoxy pentyl, 2-methoxy hexyl, 2-methoxy heptyl, 2-methoxy octyl, 2-methoxy nonyl, decyl, 2-methoxy undecyl, 2-methoxy dodecyl, 2-methoxy tridecyl, 2-methoxy tetradecyl, 2-methoxy pentadecyl, 2-methoxy hexadecyl, 2-methoxy heptadecyl, 2-methoxy octadecyl, 2-methoxy nonadecyl, 2-methoxy eicosyl, 2-methoxy henicosyl, 2-methoxy docosyl, 2-methoxy tricosyl, 2-methoxy tetracosyl, 1-acetoxy methyl, 1-acetoxy ethyl, 1-acetoxy propyl, 1-acetoxy butyl, 1-acetoxy pentyl, 1-acetoxy hexyl, 1-acetoxy heptyl, 1-acetoxy octyl, 1-acetoxy nonyl, decyl, 1-acetoxy undecyl, 1-acetoxy dodecyl, 1-acetoxy tridecyl, 1-acetoxy tetradecyl, 1-acetoxy pentadecyl, 1-acetoxy hexadecyl, 1-acetoxy heptadecyl, 1-acetoxy octadecyl, 1-acetoxy nonadecyl, 1-acetoxy eicosyl, 1-acetoxy henicosyl, 1-acetoxy docosyl, 1-acetoxy tricosyl, 1-acetoxy tetracosyl, 1-cyano methyl, 1-cyano ethyl, 1-cyano propyl, 1-cyano butyl, 1-cyano pentyl, 1-cyano hexyl, 1-cyano heptyl, 1-cyano octyl, 1-cyano nonyl, decyl, 1-cyano undecyl, 1-cyano dodecyl, 1-cyano tridecyl, 1-cyano tetradecyl, 1-cyano pentadecyl, 1-cyano hexadecyl, 1-cyano heptadecyl, 1-cyano octadecyl, 1-cyano nonadecyl, 1-cyano eicosyl, 1-cyano henicosyl, 1-cyano docosyl, 1-cyano tricosyl, 1-cyano tetracosyl, 2-cyano propyl, 2-cyano butyl, 2-cyano pentyl, 2-cyano hexyl, 2-cyano heptyl, 2-cyano octyl, 2-cyano nonyl, decyl, 2-cyano undecyl, 2-cyano dodecyl, 2-cyano tridecyl, 2-cyano tetradecyl, 2-cyano pentadecyl, 2-cyano hexadecyl, 2-cyano heptadecyl, 2-cyano octadecyl, 2-cyano nonadecyl, 2-cyano eicosyl, 2-cyano henicosyl, 2-cyano docosyl, 2-cyano tricosyl, 2-cyano tetracosyl, 1-thioyl methyl, 1-thioyl ethyl, 1-thioyl propyl, 1-thioyl butyl, 1-thioyl pentyl, 1-thioyl hexyl, 1-thioyl heptyl, 1-thioyl octyl, 1-thioyl nonyl, decyl, 1-thioyl undecyl, 1-thioyl dodecyl, 1-thioyl tridecyl, 1-thioyl tetradecyl, 1-thioyl pentadecyl, 1-thioyl hexadecyl, 1-thioyl heptadecyl, 1-thioyl octadecyl, 1-thioyl nonadecyl, 1-thioyl eicosyl, 1-thioyl henicosyl, 1-thioyl docosyl, 1-thioyl tricosyl and 1-thioyl tetracosyl.

In a preferred embodiment, the term alkenyl denotes unsubstituted, linear $C_2$-$C_{24}$ alkenyl which is preferably selected from the group consisting of 1-propenyl, 1-butenyl, 1-pentenyl, 1-hexenyl, 2-hexenyl, 1-heptenyl, 2-heptenyl, 1-octenyl, 2-octenyl, 1-nonenyl, 2-nonenyl, 1-decenyl, 2-decenyl, 1-undecenyl, 2-undecenyl, 1-dodecenyl, 2-dodecenyl, 1-tridecenyl, 2-tridecenyl, 1-tetradecenyl, 2-tetradecenyl, 1-pentadecenyl, 2-pentadecenyl, 1-hexadecenyl, 2-hexadecenyl, 1-heptadecenyl, 2-heptadecenyl, 1-octadecenyl, 2-octadecenyl, 1-nonadecenyl, 2-nonadecenyl, 1-eicosenyl and 2-eicosenyl, more preferably selected from 1-hexenyl, 2-hexenyl, 1-heptenyl, 2-heptenyl, 1-octenyl, 2-octenyl, 1-nonenyl, 2-nonenyl, 1-decenyl, 2-decenyl, 1-undecenyl, 2-undecenyl, 1-dodecenyl, 2-dodecenyl, 1-tridecenyl, 2-tridecenyl, 1-tetradecenyl, 2-tetradecenyl, 1-pentadecenyl, 2-pentadecenyl, 1-hexadecenyl, 2-hexadecenyl, 1-heptadecenyl, 2-heptadecenyl, 1-octadecenyl, 2-octadecenyl, 1-nonadecenyl, 2-nonadecenyl, 1-eicosenyl and 2-eicosenyl, 20-henicosenyl, 2-docosenyl, 6-tricosenyl and 2-tetracosenyl.

In a preferred embodiment, the unsubstituted branched $C_2$-$C_{24}$ alkenyl is selected from the group consisting of isopropenyl, iso-butenyl, neo-pentenyl, 2-ethyl-hexenyl, 2-propyl-heptenyl, 2-butyl-octenyl, 2-pentyl-nonenyl, 2-hexyl-decenyl, iso-hexenyl, iso-heptenyl, iso-octenyl, iso-nonenyl, iso-decenyl, iso-dodecenyl, iso-tetradecenyl, iso-hexadecenyl, iso-octadecenyl, iso-eicosenyl, 2-methyl tricosenyl, 2-ethyl docosenyl, 3-ethylhenicosenyl, 3-ethyl icosenyl, 4-propylhenicosenyl, 4-propylnonadecenyl, 6-butyldodecenyl, 5-ethylundedcenyl, 1,4-hexadienyl, 1,3-hexadienyl, 2,5-hexadienyl, 3,5-hexadienyl, 2,4-hexadienyl, 1,3,5-hexatrienyl, 1,3,6-heptatrienyl, 1,4,7-octatrienyl or 2-methyl-1,3,5hexatrienyl, 1,3,5,7-octatetraenyl, 1,3,5,8-nonatetraenyl, 1,4,7,10-undecatetraenyl, 2-ethyl-1,3,6,8-nonatetraenyl, 2-ethenyl-1,3,5,8-nonatetraenyl, 1,3,5,7,9-decapentaenyl, 1,4,6,8,10-undecapentaenyl and 1,4,6,9,11-dodecapentaenyl.

In a preferred embodiment, the substituted, linear or branched $C_2$-$C_{24}$ alkenyl refers to a branched or a linear unsaturated hydrocarbon group having $C_2$-$C_{24}$ carbon atoms substituted with functional groups selected from, hydroxy, alkoxy, C(═O)—R, CN and SR; wherein R is hydrogen, substituted or unsubstituted, linear or branched $C_1$-$C_{24}$ alkyl, substituted or unsubstituted, linear or branched $C_2$-$C_{24}$alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl, substituted or unsubstituted $C_7$-$C_{24}$ arylalkyl.

In a preferred embodiment the substituted, linear or branched $C_2$-$C_{24}$ alkenyl refers to a branched or an linear unsaturated hydrocarbon group having $C_2$-$C_{24}$carbon atoms substituted with functional groups selected from hydroxy, alkoxy, C(═O)—R, CN and SR; preferably selected from the group consisting of 2-hydroxy propenyl, 3-hydroxy butenyl, 3-hydroxy pentenyl, 5-hydroxy hexenyl, 7-hydroxy heptenyl, 3-hydroxy octenyl, 5-hydroxy nonenyl, decyl, 11-hydroxy undecenyl, 9-hydroxy dodecenyl, 6-hydroxy tridecenyl, 4-hydroxy tetradecenyl, 6-hydroxy pentadecenyl, 3-hydroxy hexadecenyl, 2-hydroxy heptadecenyl, 7-hydroxy octadecenyl, 6-hydroxy nonadecenyl, 4-hydroxy eicosenyl, 2-hydroxy henicosenyl, 3-hydroxy docosenyl, 2-hydroxy tricosenyl, 23-hydroxy tetracosenyl, 1-methoxy ethenyl, 2-methoxy propenyl, 4-methoxy butenyl, 3-methoxy pentenyl, 5-methoxy hexenyl, 2-methoxy heptenyl, 5-methoxy octenyl, 3-methoxy nonenyl, 6-methoxy undecenyl, 1-methoxy dodec-2-enyl, 1-methoxy tridec-5-enyl, 3-methoxy tetradic-5-enyl, 3-methoxy pentade-12-encyl, 10-methoxy hexadec-15-enyl, 12-methoxy heptadic-16-enyl, 1-methoxy octadec-3-enyl, 1-methoxy nonadec-2-enyl, 1-methoxy eicos-20-enyl, 1-methoxy henicos-2-enyl, 1-methoxy docos-4-enyl, 1-methoxy tricos-22-enyl, 1-methoxy tetracos-23-enyl, 2-methoxy prop-1-enyl, 2-methoxy but-1-enyl, 2-methoxy pent-4-enyl, 2-methoxy hex-2-enyl, 2-methoxy hept-3-enyl, 2-methoxy oct-7-enyl, 2-methoxy non-5-enyl, 2-methoxy undec-10-enyl, 2-methoxy dodec-4-enyl, 2-methoxy tridec-12-enyl, 2-methoxy tetradic-10-enyl, 2-methoxy pentadec-14-enyl, 2-methoxy hexadec-1-enyl, 2-methoxy heptadic-1-enyl, 2-methoxy octadic-12-enyl, 2-methoxy nonadec-10-enyl, 2-methoxy eicos-18-enyl, 2-methoxy henicos-2-enyl, 2-methoxy docos-3-enyl, 20-methoxy tricos-2-enyl, 21-methoxy tetracos-4-enyl, 1-acetoxy ethenyl, 1-acetoxy prop-1-enyl, 1-acetoxy but-2-enyl, 1-acetoxy pent-4-enyl, 1-acetoxy hex-2-enyl, 1-acetoxy hept-1-enyl, 1-acetoxy oct-7-enyl, 1-acetoxy non-2-enyl, 5-acetoxy dec-3-enyl, 1-acetoxy undec-10-enyl, 1-acetoxy dodec-2-enyl, 1-acetoxy tridec-12-enyl, 10-acetoxy tetradec-2-enyl, 15-acetoxy pentadec-2-enyl, 10-acetoxy hexadec-2-enyl, 11-acetoxy heptadec-1-enyl, 13-acetoxy octadec-2-enyl, 1-acetoxy nonadec-14-enyl, 20-acetoxy eicos-19-enyl, 1-acetoxy henicos-2-enyl, 1-acetoxy docos-10-enyl, 1-acetoxy tricos-22-enyl, 1-acetoxy tetracos-23-enyl, 1-cyano eth-1-enyl, 1-cyano prop-2-enyl, 1-cyano but-2-enyl, 1-cyano pent-3-enyl, 1-cyano hex-5-enyl, 1-cyano hept-6-enyl, 1-cyano oct-2-enyl, 1-cyano non-3-enyl, 11-cyano undec-2-enyl, 10-cyano dodec-2-enyl, 10-cyano tridec-12-enyl, 1-cyano tetradec-3-enyl, 1-cyano pentadec-14-enyl, 1-cyano hexadec-15-enyl, 1-cyano heptadec-2-enyl, 1-cyano octadec-3-enyl, 1-cyano nonadec-18-enyl, 1-cyano eicos-10-enyl, 1-cyano henicos-20-enyl, 15-cyano docos-3-enyl, 1-cyano tricos-20-enyl, 1-cyano tetracos-2-enyl, 2-cyano prop-2-enyl, 2-cyano but-1-enyl, 2-cyano pent-1-enyl, 2-cyano hex-3-enyl, 2-cyano hept-6-enyl, 2-cyano oct-1-enyl, 2-cyano non-8-enyl, 2-cyano undec-10-enyl, 2-cyano dodec-1-enyl, 2-cyano tridec-12-enyl, 2-cyano tetradec-10-enyl, 2-cyano pentadec-3-enyl, 2-cyano hexadec-2-enyl, 2-cyano heptadec-1-enyl, 2-cyano octadec-12-enyl, 2-cyano nonadec-15-enyl, 2-cyano eicos-1-enyl, 2-cyano henicos-5-enyl, 2-cyano docos-20-enyl, 2-cyano tricos-22-enyl, 2-cyano tetracos-20-enyl, 1-thionyl eth-1-enyl, 1-thionyl prop-2-enyl, 1-thionyl but-2-enyl, 1-thionyl pent-4-enyl, 1-thionyl hex-2-enyl, 1-thionyl hept-5-enyl, 1-thionyl oct-3-enyl, 1-thionyl non-5-enyl, 1-thionyl undec-10-enyl, 1-thionyl dodec-11-enyl, 1-thionyl tridec-2-enyl, 1-thionyl tetradec-4-enyl, 1-thionyl pentadec-5-enyl, 1-thionyl hexadec-3-enyl, 1-thionyl heptadec-2-enyl, 1-thionyl octadec-3-enyl, 1-thionyl nonadec-15-enyl, 1-thionyl eicos-18-enyl, 1-thionyl henicos-20-enyl, 1-thionyl docos-21-enyl, 1-thionyl tricos-20-enyl and 1-thionyl tetracos-22-enyl.

In a preferred embodiment, the substituted or unsubstituted $C_5$-$C_{24}$ cycloalkyl refers to a monocyclic and bicyclic 5- to 24-membered saturated cycloaliphatic radical. Representative examples of unsubstituted or branched $C_5$-$C_{24}$ monocyclic and bicyclic cycloalkyl include, but are not limited to, cyclopentyl, cyclohexyl, cycloheptyl, cyclooctyl, bicyclo[2.2.1]heptyl, and bicyclo[3.1.1]heptyl.

In another preferred embodiment, the $C_5$-$C_{24}$ monocyclic and bicyclic cycloalkyl can be further branched with one or more equal or different alkyl groups such as methyl, ethyl, n-propyl, iso-propyl, n-butyl, iso-butyl, n-pentyl, iso-pentyl, neo-pentyl etc. The representative examples of branched $C_3$-$C_{10}$ monocyclic and bicyclic cycloalkyl include, but are not limited to, methyl cyclohexyl and dimethyl cyclohexyl.

In a preferred embodiment, the unsubstituted or substituted $C_5$-$C_{24}$ cycloalkenyl refers to a monocyclic and bicyclic 5- to 24-membered unsaturated cycloaliphatic radical which comprises one or more double bonds. Representative examples of $C_5$-$C_{24}$ cycloalkenyl include, but are not limited to, cyclopentenyl, cyclohexenyl, cycloheptenyl, cyclooctenyl, cyclononenyl or cyclodecenyl. These radicals can be branched with one or more equal or different alkyl radical, preferably with methyl, ethyl, n-propyl or iso-propyl. The representative examples of branched $C_5$-$C_{24}$ monocyclic and bicyclic cycloalkenyl include, but are not limited to, methyl cyclohexenyl and dimethyl cyclohexenyl.

In a preferred embodiment, the substituted or unsubstituted $C_6$-$C_{24}$ aryl may have more than one aromatic ring. The representative examples for substituted and unsubstituted $C_6$-$C_{24}$ aryl include phenyl, naphthyl, anthracenyl, tetraphenyl, phenalenyl and phenanthrenyl.

In a preferred embodiment, the substituted $C_6$-$C_{24}$ aryl refers to an aromatic ring having substitution at different positions. The $C_6$-$C_{24}$ aryl may have more than one aromatic ring. The representative examples for substituted and unsubstituted $C_6$-$C_{24}$ aryl include tolyl, xylyl, 2-hydroxyphenyl, 2,3-dihydroxyphenyl, 2-methoxy phenyl, 2-hydroxy-4-methoxyphenyl, 2,4-dimethoxyphenyl, 2-chlorophenyl, 2-chloro-4-hydroxyphenyl, 2-chloro-4-methoxy phenyl, 3-chloro-4-methoxyphenyl, 2-methyl-4-methoxy-6-chlorophenyl and 2-acetyl-4-hydroxyphenyl.

In a preferred embodiment, the "arylalkyl" refers to an aryl ring attached to an alkyl chain. The representative examples for the arylalkyl include, but are not limited to, 1-phenylmethyl, 1-phenylethyl, 1-phenylpropyl, 1-phenylbutyl, 1-methyl-1-phenyl-propyl, 3-phenylpropyl, 4-phenylbutyl, 3-phenylbutyl and 2-methyl-3-phenyl-propyl.

The representative example for C(═O)—R include C(═O)—$CH_3$, C(═O)—$C_2H_5$, C(═O)—$C_3H_7$, C(═O)—$C_4H_9$, C(═O)—$C_4H_7$, C(═O)—$C_6H_{11}$, C(═O)—$C_6H_9$, C(═O)—$C_9H_{19}$, C(═O)—$C_{10}H_{19}$, C(═O)$C_{10}H_{21}$, C(═O)—$C_{15}H_{31}$, C(═O)—$C_{13}H_{27}$, C(═O)—$C_{14}H_{29}$, C(═O)—$C_{15}H_{31}$ and C(═O)—$C_{20}H_{41}$.

The representative examples for OR include $OCH_3$, $OC_2H_5$, $OC_3H_7$, $OC_4H$, $OC_4H_7$, $OC_5H_{11}$, $OC_6H_{11}$, $OC_6H_9$, $OC_7H_{15}$, $OC_8H_{17}$, $OC_9H_{19}$, $OC_{10}H_{19}$, $OC_{10}H_{21}$, $OC_{15}H_{31}$, $OC_{13}H_{27}$, $OC_{14}H_{29}$, $OC_{15}H_{31}$ and $OC_{20}H_{41}$.

In a preferred embodiment, wherein R and R' in N—RR' are independently selected from the group consisting of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl eicosyl, henicosyl, docosyl, tricosyl, tetracosyl, isopropyl, iso-butyl, neo-pentyl, 2-ethyl-hexyl, 2-propyl-heptyl, 2-butyl-octyl, 2-pentyl-nonyl, 2-hexyl-decyl, iso-hexyl, iso-heptyl, iso-octyl, iso-nonyl, iso-decyl, iso-dodecyl, iso-tetradecyl, iso-hexadecyl, iso-octadecyl and iso-eicosyl. The representative example for —N—RR' include —$N(CH_3)_2$, —$N(C_2H_5)_2$, —$N(C_3H_7)_2$, —$N(C_4H_9)_2$, —$N(C_4H_7)_2$, —$N(C_6H_{11})_2$, —$N(C_6H_9)_2$, —$N(C_9H_{19})_2$, —$N(C_{10}H_{19})_2$, —$N(C_{10}H_{21})_2$, —$N(C_{15}H_{31})_2$, —$N(C_{13}H_{27})_2$, —$N(C_{14}H_{29})_2$, —$N(C_{15}H_{31})_2$ and —$N(C_{20}H_{41})_2$.

In a preferred embodiment, in C(═O)—NRR', wherein R and R' are independently selected from the group consisting of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl eicosyl, henicosyl, docosyl, tricosyl, tetracosyl, isopropyl, iso-butyl, neo-pentyl, 2-ethyl-hexyl, 2-propyl-heptyl, 2-butyl-octyl, 2-pentyl-nonyl, 2-hexyl-decyl, iso-hexyl, iso-heptyl, iso-octyl, iso-nonyl, iso-decyl, iso-dodecyl, iso-tetradecyl, iso-hexadecyl, iso-octadecyl and iso-eicosyl. The representative example for C(═O)—N—RR' include C(═O)—$N(CH_3)_2$, C(═O)—$N(C_2H)_2$, C(═O)—$N(C_3H_7)_2$, C(═O)—$N(C_4H_9)_2$, C(═O)—$N(C_4H_7)_2$, C(═O)—$N(C_6H_{11})_2$, C(═O)—$N(C_6H_9)_2$, C(═O)—$N(C_9H_{19})_2$, C(═O)—$N(C_{10}H_{19})_2$, C(═O)—$N(C_{10}H_{21})_2$, C(═O)—$N(C_{15}H_{31})_2$, C(═O)—$N(C_{13}H_{27})_2$, C(═O)—$N(C_{14}H_{29})_2$, C(═O)—$N(C_{15}H_{31})_2$ and C(═O)—$N(C_{20}H_{41})_2$.

The representative examples for OR include $OCH_3$, $OC_2H_5$, $OC_3H_7$, $OC_4H_9$, $OC_4H_7$, $OC_6H_{11}$, $OC_6H_{11}$, $OC_6H_9$, $OC_7H_{15}$, $OC_8H_{17}$, $OC_9H_{19}$, $OC_{10}H_{19}$, $OC_{10}H_{21}$, $OC_{15}H_{31}$, $OC_{13}H_{27}$, $OC_{14}H_{29}$, $OC_{15}H_{31}$ and $OC_{20}H_{41}$.

In another preferred embodiment, the moieties of formula (c1) is formula (c1)

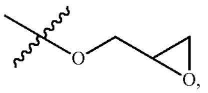

In another preferred embodiment, the moieties of formula (c2) is selected from the group consisting of —O(C═O)CH═$CH_2$, —O(C═O)$C(CH_3)$═$CH_2$, —O(C═O)CH═$CH(CH_3)$, —O(C═O)CH═$(CH_3)_2$, and O(C═O)C$(CH_3)$═$(CH_3)_2$.

In another preferred embodiment, the compound of formula (D1) is selected form the group consisting of 2,4,6-trichloro-1,3,5-triazine, 2,4,6-tribromo-1,3,5-triazine, 2,4,6-triiodo-1,3,5-triazine, 2-bromo-4,6-dichloro-1,3,5-triazine; more preferably 2,4,6-trichloro-1,3,5-triazine.

In another preferred embodiment, the compound of formula (D2) is selected form the group consisting of 2,4-dichloro-6-(4-methoxyphenyl)-1,3,5-triazine, 2,4-dichloro-6-(4-methylphenyl)-1,3,5-triazine, 2,4-dichloro-6-(4-phenylphenyl)-1,3,5-triazine, 2-(4,6-dichloro-1,3,5-triazin-2-yl)-5-(oxiran-2-ylmethoxy)phenol, 2-(4,6-dichloro-1,3,5-triazin-2-yl)-5-hexoxy-phenol, 2-(4,6-dichloro-1,3,5-triazin-2-yl)-5-(2-ethylhexoxy)phenol, 2,4-dichloro-6-phenyl-1,3,5-triazine, 4-(4,6-dichloro-1,3,5-triazin-2-yl)benzene-1,3-diol, 2-(4,6-dichloro-1,3,5-triazin-2-yl)-5-(3-dodecoxy-2-hydroxy-propoxy)phenol, 2-(4,6-dichloro-1,3,5-triazin-2-yl)-5-(3-tridecoxy-2-hydroxy-propoxy)phenol, 2,4-dichloro-6-(2,4-dimethylphenyl)-1,3,5-triazine, 2-(2-methylprop-2-enoyloxy)ethyl 4-(4,6-dichloro-1,3,5-triazin-2-yl)benzoate, 2-prop-2-enoyloxyethyl 4-(4,6-dichloro-1,3,5-triazin-2-yl)benzoate, 15-[4-(4,6-dichloro-1,3,5-triazin-2-yl)phenoxy]pentadecane-1,4,7-triol, 15-[4-(4,6-dichloro-1,3,5-triazin-2-yl)-3-hydroxyphenoxy]pentadecane-1,4,7-triol, [9-[4-(4,6-dichloro-1,3,5-triazin-2-yl)-3-hydroxyphenoxy]-1-(3,6-disulfooxyhexyl)nonyl] hydrogen sulfate, [15-[4-(4,6-dichloro-1,3,5-triazin-2-yl)-3-hydroxy-phenoxy]-4,7-di(prop-2-enoyloxy)pentadecyl] prop-2-enoate, 2,4-dichloro-6-(2,4-dibutoxyphenyl)-1,3,5-triazine and 2-(4,6-dichloro-1,3,5-triazin-2-yl)-5-[9,12,15-tris(oxiran-2-ylmethoxy)pentadecoxy]phenol.

In another preferred embodiment, the compound of formula (D3) is selected form the group consisting of 4-[4-chloro-6-(2,4-dihydroxyphenyl)-1,3,5-triazin-2-yl]benzene-1,3-diol, 2-chloro-4,6-bis(2,4-dimethylphenyl)-1,3,5-triazine, 2-chloro-4,6-bis(4-methoxyphenyl)-1,3,5-triazine, 2-chloro-4,6-bis(4-phenylphenyl)-1,3,5-triazine, 2-[4-chloro-6-(2-hydroxy-4-pentadecoxy-phenyl)-1,3,5-triazin-2-yl]-5-pentadecoxy-phenol, 2-[4-chloro-6-[2-hydroxy-4-

[9,12,15-tris(oxiran-2-ylmethoxy)pentadecoxy]phenyl]-1,3,5-triazin-2-yl]-5-[9,12,15-tris(oxiran-2-ylmethoxy)pentadecoxy]phenol, [15-[4-[4-chloro-6-[2-hydroxy-4-[9,12,15-tri(prop-2-enoyloxy)pentadecoxy]phenyl]-1,3,5-triazin-2-yl]-3-hydroxy-phenoxy]-4,7-di(prop-2-enoyloxy)pentadecyl] prop-2-enoate, [9-[4-[4-chloro-6-[2-hydroxy-4-(9,12,15-trisulfooxypentadecoxy)phenyl]-1,3,5-triazin-2-yl]-3-hydroxy-phenoxy]-1-(3,6-disulfooxyhexyl)nonyl] hydrogen sulfate, 5-butoxy-2-[4-(4-butoxy-2-hydroxy-phenyl)-6-chloro-1,3,5-triazin-2-yl]phenol and 15-[4-[4-chloro-6-[2-hydroxy-4-(9,12,15-trihydroxypentadecoxy)phenyl]-1,3,5-triazin-2-yl]-3-hydroxy-phenoxy]pentadecane-1,4,7-triol.

In another preferred embodiment, the compound of formula (E) is selected form the group consisting of 3-dodecylphenol, 3-tridecylphenol, 3-tetradecylphenol, 3-pentadecylphenol, 3-hexadecylphenol and 5-(8,11,14-pentadecatrienyl) phenol.

In another preferred embodiment, the compound of formula (G) is selected form the group consisting of 4-methoxy benzene, 3-methoxyphenol, 4-methyl benzene, 3-methyl phenol, biphenyl, 3-(oxiran-2-ylmethoxy) phenol, benzene-1,3-diol, 3-hexoxyphenol, 3-(2-ethylhexoxy) phenol, benzene, 3-(3-dodecoxy-2-hydroxy-propoxy)phenol, [2-hydroxy-3-(3-hydroxyphenoxy)propyl] prop-2-enoate, 3-(3-hydroxyphenoxy)propane-1,2-diol, 3-(3-tridecoxy-2-hydroxy-propoxy)phenol, m-xylene, 2-(2-methylprop-2-enoyloxy)ethyl benzoate, 2-prop-2-enoyloxyethyl benzoate and 15-phenoxypentadecane-1,4,7-triol.

In another preferred embodiment, the at least one acid is selected from the group consisting of mineral acids, Lewis acids, sulfonic acids and acidic ion exchange resins; more preferably the at least one acid is selected from the group consisting of mineral acids and Lewis acids.

In another preferred embodiment, the at least one mineral acid is selected from the group consisting of sulfuric acid, hydrochloric acid, phosphoric acid, perchloric acid, nitric acid, nitrous acid, sulphurous acid, chloric acid, chlorous acid and hypochlorous acid.

In another preferred embodiment, the at least one Lewis acid is selected from the group consisting of $AsX_3$, $GaX_3$, $BX_3$, $BX_3.(C_2H_5)_2O$, $BX_3.S(CH_3)_2$, $AlX_3$, $(C_2H)_2AlX$, $SbX_3$, $SbX_5$, $SnX_2$, $MgX_2$, $MgX_2.O(C_2H_5)_2$, $ZnX_2$, $BiX_3$, $FeX_2$, $TiX_2$, $TiX_4$, $NbX_5$, $NiX_2$, $CoX_2$, $HgX_2$, $PbX_2$, $MnX_2$, CuX, $CuX_2$ whereby X in each case denotes F, Cl, Br, $CF_3—S(═O)_2O$, $CH_3—S(═O)_2O$, or I; $BH_3$, $B(CH_3)_3$, $GaH_3$, $AlH_3$, $Al(acetate)(OH)_2$, $Al[OCH(CH_3)_2]_3$, $Al(OCH_3)_3$, $Al(OC_2H_5)_3$, $Al_2O_3$, $(CH_3)_3Al$, $Ti[OCH(CH_3)_2]_3Cl$, $Ti[OCH(CH_3)_2]_4$, methylaluminum di-(2,6-di-tert-butyl-4-methylphenoxide), methylaluminum di-(4-brom-2,6-di-tert-butylphenoxide), $LiClO_4$; $Mg(acetate)_2$, $Zn(acetate)_2$, $Ni(acetate)_2$, $Ni(NO_3)_2$, $Co(acetate)_2$, $Co(NO_3)_2$, $Cu(acetate)_2$, $Cu(NO_3)_2$, Li(acetate), $Zr(acetylacetonate)_4$, $Si(acetate)_4$, K(acetate), Na(acetate), Cs(acetate), Rb(acetate), $Mn(acetate)_2$, $Fe(acetate)_2$, $Bi(acetate)_3$, $Sb(acetate)_3$, $Sr(acetate)_2$, $Sn(acetate)_2$, $Zr(acetate)_2$, $Ba(acetate)_2$, $Hg(acetate)_2$, Ag(acetate), $Tl(acetate)_3$, $Sc(trifluoromethanesulfonate)_3$, $Ln(trifluoromethanesulfonate)_3$, $Ni(trifluoromethanesulfonate)_2$, $Ni(tosylate)_2$, $Co(trifluoromethanesulfonate)_2$, $Co(tosylate)_2$, $Cu(tri\text{-}fluoromethanesulfonate)_2$ and $Cu(tosylate)_2$; more preferably the Lewis acid is selected from the group consisting of $AsX_3$, $GaX_3$, $BX_3$, $BX_3.(C_2H_5)_2O$, $BX_3.S(CH_3)_2$, $AlX_3$, $(C_2H)_2AlX$, $SbX_3$, $SbX_5$, $SnX_2$, $MgX_2$, $MgX_2.O(C_2H_5)_2$, $ZnX_2$, $BiX_3$, $FeX_2$, $TiX_2$, $TiX_4$, $NbX_5$, $NiX_2$, $CoX_2$, $HgX_2$, $PbX_2$, $MnX_2$, CuX, $CuX_2$ whereby X in each case denotes F, Cl, Br, $CF_3—S(═O)_2O$, $CH_3—S(═O)_2O$, or I; most preferably selected from the group consisting of $BX_3$, $BX_3.(C_2H_5)_2O$, $BX_3.S(CH_3)_2$, $AlX_3$, $(C_2H_5)_2AlX$, $TiX_2$, $TiX_4$ whereby X in each case denotes F, Cl, Br, $S(═O)_3$, $CF_3—S(═O)_2O$, $CH_3—S(═O)_2O$, or I; particularly preferably, selected from the group consisting of $BX_3$, $AlX_3$, $(C_2H_5)_2AlX$, whereby X in each case denotes F, Cl, Br, $CF_3—S(═O)_2O$, $CH_3—S(═O)_2O$, or I.

In another preferred embodiment, the at least one Lewis acid is selected from the group consisting of $BX_3$, $BX_3.(C_2H_5)_2O$, $BX_3.S(CH_3)_2$, $AlX_3$, $ZnX_2$, $FeX_3$ and $TiX_4$, whereby X in each case denotes F, Cl, or Br; more preferably the at least one Lewis acid is selected from the group consisting of $BX_3$, $BX_3.(C_2H_5)_2O$, $BX_3.S(CH_3)_2$, $AlX_3$, whereby X in each case denotes F, Cl, or Br; most preferably the at least one Lewis acid is selected from the group consisting of $BX_3$, $BX_3.(C_2H_5)_2O$, $BX_3.S(CH_3)_2$, $AlX_3$ whereby X in each case denotes F, or Cl; and in particular the at least one Lewis acid is $AlX_3$ whereby X in each case denotes Cl.

In another preferred embodiment, the at least one sulfonic acid is selected from the group consisting of methanesulfonic acid, ethanesulfonic acid, 1-propanesulfonic acid, 1-butanesulfonic acid, trifluoromethanesulfonic acid, benzenesulfonic acid, p-toluenesulfonic acid, p-xylene-2-sulfonic acid, naphathalene-1-sulfonic acid and naphthalene-2-sulfonic acid.

In another preferred embodiment, the step i. and step ii. are carried out in presence of at least one solvent.

In another preferred embodiment, the at least one solvent is selected from the group consisting of halogenated aliphatic hydrocarbons, halogenated aromatic hydrocarbons, carbon disulphide and polar aprotic solvents; more preferably the at least one solvent is selected from the group consisting of halogenated aliphatic hydrocarbons and halogenated aromatic hydrocarbons.

In another preferred embodiment, the halogenated aliphatic hydrocarbons are selected from the group consisting of 1,1,2,2-tetrachloroethylene, 1,1-dichloroethylene and 1,2-dichloroethylene.

In another preferred embodiment, the halogenated aromatic hydrocarbons are selected from the group consisting of monochlorobenzene, 1,2-dichlorobenzene, 1,3-dischlorobenzene, 1,4-dichlorobenzene and 1,3,5-trichlorobenzene.

In another preferred embodiment, the polar aprotic solvents are selected from the group consisting of ethers, lactones, carbonates, sulfones, N,N-dimethylformamide, N,N-dimethylacetamide, acetonitrile, dimethylsulfoxide, N-methyl-pyrrolidone and N-ethyl-pyrrolidone.

In another preferred embodiment, the ethers are selected from the group consisting of methyl tert-butyl ether, dioxane, diethoxy methane, dimethoxy methane, tetrahydrofuran and tetrahydropyran.

In another preferred embodiment, the wherein in step i. the at least one acid is present in an amount in the range of ≥20 mol.-% to ≤500 mol.-%, based on the total amount of the at least one compound of formula (D); more preferably in step i. the at least one acid is present in an amount in the range of ≥50 mol.-% to ≤300 mol.-%, based on the total amount of the at least one compound of formula (D) and most preferably in step i. the at least one acid is present in an amount in the range of ≥100 mol.-% to ≤200 mol.-%, based on the total amount of the at least one compound of formula (D).

In another preferred embodiment, the step i. and step ii. are carried out at a temperature in the range of ≥50° C. to ≤150° C.; more at a temperature in the range of ≥50° C. to ≤130° C.; and most preferably at a temperature in the range of ≥70° C. to ≤130° C.

In another preferred embodiment, the step i. and step ii. are conducted for a period of 30 minutes to 24 hours.

In an embodiment, the presently claimed invention is directed to a compound of formula (A), formula (A)

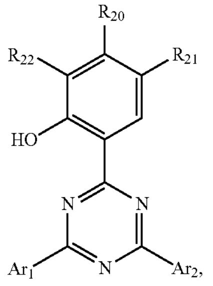

wherein $Ar_1$ and $Ar_2$ are independently of each other a moiety of the formula (B) or a moiety of the formula (J), formula (B)

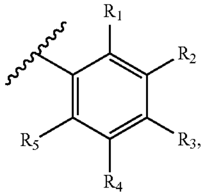

formula (J)

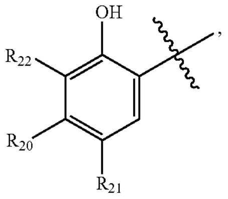

wherein $R_1$, $R_2$, $R_3$, $R_4$ and $R_5$ are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ aryl, substituted or unsubstituted $C_7$-$C_{24}$ arylalkyl, —C(═O)—R, —OR; or $R_1$ and $R_2$ together with the carbon atoms to which they are bonded or $R_2$ and $R_3$ together with the carbon atoms to which they are bonded or $R_3$ and $R_4$ together with the carbon atoms to which they are bonded or $R_4$ and $R_5$ together with the carbon atoms to which they are bonded form a saturated or unsaturated, unsubstituted or substituted 5- to 20-membered carbocyclic ring that optionally contains 1, 2 or 3 heteroatom(s) selected from O, N or S as ring member(s); and R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;

$R_{20}$ is selected from the group consisting of substituted or unsubstituted, linear or branched $C_{12}$-$C_{16}$ alkyl, substituted or unsubstituted and linear or branched $C_{12}$-$C_{16}$ alkenyl; and $R_{21}$ is selected from the group consisting of hydrogen, substituted or unsubstituted, linear or branched $C_{12}$-$C_{16}$ alkyl and substituted or unsubstituted, linear or branched $C_{12}$-$C_{16}$ alkenyl;

$R_{22}$ is selected from the group consisting of hydrogen and substituted or unsubstituted, linear or branched $C_1$-$C_6$ alkyl; or $R_{20}$ and $R_{21}$ together with the carbon atoms to which they are bonded form a saturated or unsaturated, 5- to 20-membered carbocyclic ring that is unsubstituted or substituted with 1, 2 or 3 substituents selected from the group consisting of halogen, substituted or unsubstituted, linear or branched $C_1$-$C_{24}$ alkyl, substituted or unsubstituted, linear or branched $C_2$-$C_{24}$ alkenyl and substituted or unsubstituted $C_6$-$C_{24}$ aryl, and that optionally contains 1, 2 or 3 heteroatom(s) selected from O, N or S as ring member(s);

wherein the following compounds of formula (A) are excluded: 2-[4,6-bis(2-hydroxy-4-pentadecyl-phenyl)-1,3,5-triazin-2-yl]-5-pentadecyl-phenol and 2-(4,6-diphenyl-1,3,5-triazin-2-yl)-5-pentadecylphenol; more preferably the presently claimed invention is directed to a compound of formula (A), formula (A)

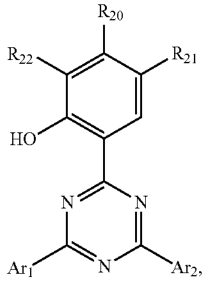

wherein $Ar_1$ and $Ar_2$ are independently of each other a moiety of the formula (B) or a moiety of the formula (J), formula (B)

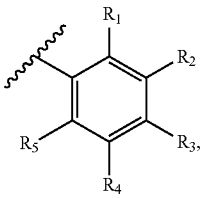

formula (J)

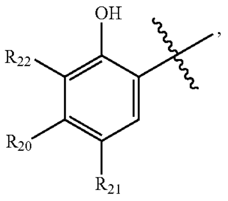

wherein $R_1$, $R_2$, $R_3$, $R_4$ and $R_5$ are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, —C(═O)—R, —OR; and R is selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;

$R_{20}$ is selected from the group consisting of substituted or unsubstituted, linear or branched $C_{12}$-$C_{16}$alkyl, substituted or unsubstituted and linear or branched $C_{12}$-$C_{16}$ alkenyl; and $R_{21}$ is selected from the group consisting of hydrogen, substituted or unsubstituted, linear or branched $C_{12}$-$C_{16}$ alkyl and substituted or unsubstituted, linear or branched $C_{12}$-$C_{16}$ alkenyl;

$R_{22}$ is selected from the group consisting of hydrogen and substituted or unsubstituted, linear or branched $C_1$-$C_6$ alkyl; or $R_{20}$ and $R_{21}$ together with the carbon atoms to which they are bonded form a saturated or unsaturated, 5- to 20-membered carbocyclic ring that is unsubstituted or substituted with 1, 2 or 3 substituents selected from the group consisting of halogen, substituted or unsubstituted, linear or branched $C_1$-$C_{24}$ alkyl, substituted or unsubstituted, linear or branched $C_2$-$C_{24}$ alkenyl and substituted or unsubstituted $C_6$-$C_{24}$ aryl, and that optionally contains 1, 2 or 3 heteroatom(s) selected from O, N or S as ring member(s);

wherein the following compounds of formula (A) are excluded: 2-[4,6-bis(2-hydroxy-4-pentadecyl-phenyl)-1,3,5-triazin-2-yl]-5-pentadecyl-phenol and 2-(4,6-diphenyl-1,3,5-triazin-2-yl)-5-pentadecylphenol;

even more preferably the presently claimed invention is directed to a compound of formula (A), formula (A)

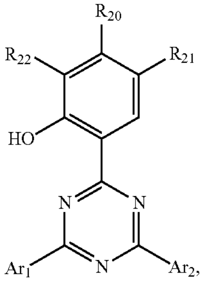

wherein $Ar_1$ and $Ar_2$ are independently of each other a moiety of the formula (B) or a moiety of the formula (J), formula (B)

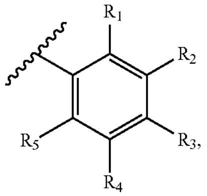

-continued formula (J)

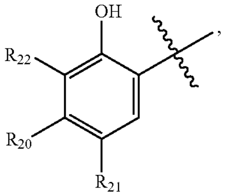

wherein $R_1$, $R_2$, $R_3$, $R_4$ and $R_5$ are independently selected from the group consisting of hydrogen, substituted or unsubstituted, linear or branched $C_1$-$C_{24}$ alkyl, substituted or unsubstituted $C_6$-$C_{24}$ aryl, substituted or unsubstituted $C_7$-$C_{24}$ arylalkyl, —OR; and R is selected from the group consisting of hydrogen, substituted or unsubstituted, linear or branched $C_1$-$C_{24}$ alkyl, substituted or unsubstituted, linear or branched $C_2$-$C_{24}$ alkenyl, and substituted or unsubstituted $C_5$-$C_{24}$ aryl;

$R_{20}$ is selected from the group consisting of substituted or unsubstituted, linear or branched $C_{12}$-$C_{16}$ alkyl, substituted or unsubstituted and linear or branched $C_{12}$-$C_{16}$ alkenyl; and $R_{21}$ is selected from the group consisting of hydrogen, substituted or unsubstituted, linear or branched $C_{12}$-$C_{16}$ alkyl and substituted or unsubstituted, linear or branched $C_{12}$-$C_{16}$ alkenyl;

$R_{22}$ is selected from the group consisting of hydrogen and substituted or unsubstituted, linear or branched $C_1$-$C_6$ alkyl; or $R_{20}$ and $R_{21}$ together with the carbon atoms to which they are bonded form a saturated or unsaturated, 5- to 20-membered carbocyclic ring that is unsubstituted or substituted with 1, 2 or 3 substituents selected from the group consisting of halogen, substituted or unsubstituted, linear or branched $C_1$-$C_{24}$ alkyl, substituted or unsubstituted, linear or branched $C_2$-$C_{24}$ alkenyl and substituted or unsubstituted $C_6$-$C_{24}$ aryl, and that optionally contains 1, 2 or 3 heteroatom(s) selected from O, N or S as ring member(s);

wherein the following compounds of formula (A) are excluded: 2-[4,6-bis(2-hydroxy-4-pentadecyl-phenyl)-1,3,5-triazin-2-yl]-5-pentadecyl-phenol and 2-(4,6-diphenyl-1,3,5-triazin-2-yl)-5-pentadecylphenol;

most preferably the presently claimed invention is directed to a compound of formula (A), formula (A)

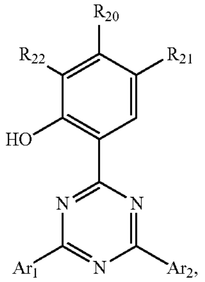

wherein $Ar_1$ and $Ar_2$ are independently of each other a moiety of the formula (B) or a moiety of the formula (J), formula (B)

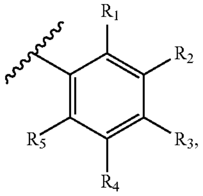

formula (J)

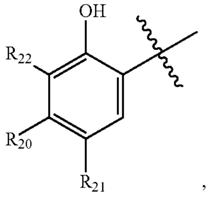

wherein $R_1$, $R_2$, $R_3$, $R_4$ and $R_5$ are independently selected from the group consisting of hydrogen, substituted or unsubstituted, linear or branched $C_1$-$C_{24}$ alkyl, substituted or unsubstituted $C_6$-$C_{24}$ aryl, —OR; and R is selected from the group consisting of hydrogen, substituted or unsubstituted, linear or branched $C_1$-$C_{24}$ alkyl, substituted or unsubstituted, linear or branched $C_2$-$C_{24}$ alkenyl, and substituted or unsubstituted $C_6$-$C_{24}$ aryl;

$R_{20}$ is selected from the group consisting of substituted or unsubstituted, linear or branched $C_{14}$-$C_{16}$alkyl, substituted or unsubstituted and linear or branched $C_{14}$-$C_{16}$ alkenyl; and $R_{21}$ is selected from the group consisting of hydrogen, substituted or unsubstituted, linear or branched $C_{14}$-$C_{16}$ alkyl and substituted or unsubstituted, linear or branched $C_{14}$-$C_{16}$ alkenyl;

$R_{22}$ is selected from the group consisting of hydrogen and substituted or unsubstituted, linear or branched $C_1$-$C_6$ alkyl;

wherein the following compounds of formula (A) are excluded: 2-[4,6-bis(2-hydroxy-4-pentadecyl-phenyl)-1,3,5-triazin-2-yl]-5-pentadecyl-phenol and 2-(4,6-diphenyl-1,3,5-triazin-2-yl)-5-pentadecylphenol;

and in particular the presently claimed invention is directed to a compound of formula (A), formula (A)

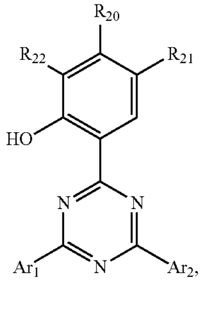

wherein $Ar_1$ and $Ar_2$ are independently of each other a moiety of the formula (B) or a moiety of the formula (J), formula (B)

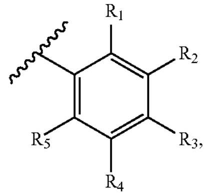

formula (J)

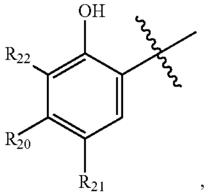

wherein $R_1$, $R_2$, $R_3$, $R_4$ and $R_5$ are independently selected from the group consisting of hydrogen, substituted or unsubstituted, linear or branched $C_1$-$C_{24}$ alkyl and substituted or unsubstituted $C_6$-$C_{10}$ aryl; and $R_{20}$ is selected from the group consisting of substituted or unsubstituted, linear or branched $C_{14}$-$C_{16}$ alkyl; and $R_{21}$ is selected from the group consisting of hydrogen, substituted or unsubstituted, linear or branched $C_{14}$-$C_{16}$ alkyl and substituted;

$R_{22}$ is selected from the group consisting of hydrogen and substituted or unsubstituted, linear or branched $C_1$-$C_6$ alkyl; wherein the following compounds of formula (A) are excluded: 2-[4,6-bis(2-hydroxy-4-pentadecyl-phenyl)-1,3,5-triazin-2-yl]-5-pentadecyl-phenol and 2-(4,6-diphenyl-1,3,5-triazin-2-yl)-5-pentadecylphenol.

In another preferred embodiment, $R_1$ is selected from the group consisting of hydrogen, halogen, substituted or unsubstituted, linear or branched $C_1$-$C_{24}$ alkyl, substituted or unsubstituted $C_6$-$C_{24}$ aryl, —C(=O)—R and OR;

$R_2$ is selected from the group consisting of hydrogen, halogen, substituted or unsubstituted, linear or branched $C_1$-$C_{24}$ alkyl, substituted or unsubstituted $C_6$-$C_{24}$ aryl, substituted or unsubstituted $C_7$-$C_{24}$ arylalkyl, —C(=O)—R, —OR, —S(=O)$_2$OH and —S(=O)$_2$OM; wherein M is an alkali metal;

$R_3$ is selected from the group consisting of hydrogen, halogen, substituted or unsubstituted, linear or branched $C_1$-$C_{24}$ alkyl, substituted or unsubstituted $C_6$-$C_{24}$ aryl, substituted or unsubstituted $C_7$-$C_{24}$ arylalkyl, —C(=O)—R, —OR, —S(=O)$_2$OH and —S(=O)$_2$OM; wherein M is an alkali metal;

$R_4$ is selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, —C(=O)R, —OR, —S(=O)$_2$—OH and —S(=O)$_2$—OM; wherein M is an alkali metal; and $R_5$ is selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, —C(=O)R, —OR, —S(=O)$_2$OH and —S(=O)$_2$OM; wherein M is an alkali metal;

R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;

wherein, in case of substitution, $C_1$-$C_{24}$ alkyl and $C_2$-$C_{24}$ alkenyl are substituted with 1, 2 or 3 substituents selected from the group consisting of —CN, $NH_2$, —N($C_1$-$C_5$ alkyl)$_2$, —N($C_1$-$C_5$-alkyl)(phenyl), —N($C_1$-$C_5$ alkyl)($CH_2$phenyl), —N($C_1$-$C_5$-alkyl)($CH_2$—$CH_2$-phenyl), —O—$CF_3$, —SH, —C(═O)—H, —C(═O)—$C_1$-$C_5$-alkyl, —O—C(═O)—$C_1$-$C_5$-alkenyl, —C(═O)-phenyl, —C(═O)—OH, —C(═O)O—($C_1$-$C_5$-alkyl), —C(═O)—O-phenyl, —C(═O)—$NH_2$, —C(═O)—NH—($C_1$-$C_5$-alkyl), —C(═O)—N($C_1$-$C_5$-alkyl)$_2$, and unsubstituted $C_6$-$C_{24}$ aryl;

$C_5$-$C_{24}$ cycloalkyl and $C_5$-$C_{24}$ cycloalkenyl are substituted with 1, 2 or 3 substituents selected from the group consisting of unsubstituted, linear or branched $C_1$-$C_{24}$ alkyl, unsubstituted, linear or branched $C_2$-$C_{24}$ alkenyl, CN, $NH_2$, —N($C_1$-$C_5$ alkyl)$_2$, —N($C_1$-$C_5$-alkyl)(phenyl), —N($C_1$-$C_5$ alkyl)($CH_2$phenyl), —N($C_1$-$C_5$-alkyl)($CH_2$—$CH_2$-phenyl), —O—$CF_3$, —SH, —C(═O)—H, —C(═O)—$C_1$-$C_5$-alkyl, —C(═O)-phenyl, —C(═O)—OH, —C(═O)—O—($C_1$-$C_5$-alkyl), —C(═O)—O-phenyl, —C(═O)—$NH_2$, —C(═O)—NH—($C_1$-$C_5$-alkyl), —C(═O)—N($C_1$-$C_5$-alkyl)$_2$, and unsubstituted $C_6$-$C_{24}$ aryl and unsubstituted $C_6$-$C_{24}$ aryl;

$C_6$-$C_{24}$ aryl and $C_7$-$C_{24}$ arylalkyl are substituted with 1, 2 or 3 substituents selected from the group consisting of halogens, —CN, —S(═O)$_2$OH, —OH, —O($C_1$-$C_5$ alkyl), —O-(phenyl), —O—($CH_2$phenyl), —O—($CH_2$—$CH_2$-phenyl), —S(═O)$_2$OM, $CH_3$, $C_2H$, $C_3H_7$, $C_8H_{17}$, $C_{15}H_{31}$, —$NH_2$, —O—$CF_3$, —SH, —N($C_1$-$C_5$ alkyl)$_2$, —N($C_1$-$C_3$-alkyl)(phenyl), —N($C_1$-$C_5$ alkyl)($CH_2$phenyl), —N($C_1$-$C_5$-alkyl)($CH_2$—$CH_2$-phenyl), —C(═O)—H, —C(═O)—$C_1$-$C_5$-alkyl, —C(═O)-phenyl, —C(═O)—OH, —C(═O)O—($C_1$-$C_5$-alkyl), —C(═O)—O-phenyl, —C(═O)—$NH_2$, —C(═O)—NH—($C_1$-$C_5$-alkyl), —C(═O)—N($C_1$-$C_5$-alkyl)$_2$, and unsubstituted $C_6$-$C_{24}$ aryl;

$R_{20}$ is selected from the group consisting of linear or branched $C_{12}$-$C_{16}$ alkyl and linear or branched $C_{12}$-$C_{16}$ alkenyl; which are in each case unsubstituted or substituted with 1, 2 or 3 substituents selected from the group consisting of —OR, —S(═O)$_2$OH, —S(═O)$_2$OM, and —O—C(═)—R, wherein M is an alkali metal;

R is selected from the group consisting of hydrogen, unsubstituted, linear or branched $C_1$-$C_{24}$ alkyl, unsubstituted, linear or branched $C_2$-$C_{24}$ alkenyl, unsubstituted $C_5$-$C_{24}$ cycloalkyl, unsubstituted $C_5$-$C_{24}$ cycloalkenyl, unsubstituted $C_6$-$C_{24}$ aryl and unsubstituted $C_7$-$C_{24}$ arylalkyl;

$R_{21}$ is selected from the group consisting of hydrogen, linear or branched $C_{12}$-$C_{16}$ alkyl and linear or branched $C_{12}$-$C_{16}$ alkenyl; which are in each case unsubstituted or substituted with 1, 2 or 3 substituents selected from the group consisting of —OR, —S(═O)$_2$OH, —S(═O)$_2$OM, and —O—C(═O)—R, moieties of formula (c1) and moieties of formula (c2), formula (c1)

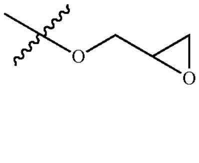

-continued formula (c2)

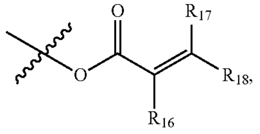

wherein M is an alkali metal;

R, $R_{16}$, $R_{17}$ and $R_{18}$ are independently selected from the group consisting of hydrogen, unsubstituted, linear or branched $C_1$-$C_{24}$ alkyl, unsubstituted, linear or branched $C_2$-$C_{24}$ alkenyl, unsubstituted $C_5$-$C_{24}$ cycloalkyl, unsubstituted $C_5$-$C_{24}$ cycloalkenyl, unsubstituted $C_6$-$C_{24}$ aryl and unsubstituted $C_7$-$C_{24}$ arylalkyl;

$R_{22}$ is selected from the group consisting of hydrogen and substituted or unsubstituted, linear or branched $C_1$-$C_4$ alkyl; or $R_{20}$ and $R_{21}$ together with the carbon atoms to which they are bonded form a saturated or unsaturated, 5- to 20-membered carbocyclic ring that is unsubstituted or substituted with 1, 2 or 3 substituents selected from the group consisting of halogen, unsubstituted, linear or branched $C_1$-$C_{24}$ alkyl, unsubstituted, linear or branched $C_2$-$C_{24}$ alkenyl and unsubstituted $C_6$-$C_{24}$ aryl, and that optionally contains 1, 2 or 3 heteroatom(s) selected from O, N or S as ring member(s).

In another preferred embodiment, $R_1$ is selected from the group consisting of hydrogen substituted or unsubstituted, linear or branched $C_1$-$C_{24}$ alkyl and OR;

$R_2$ is selected from the group consisting of hydrogen, substituted or unsubstituted, linear or branched $C_1$-$C_{24}$ alkyl and OR;

$R_3$ is selected from the group consisting of hydrogen, substituted or unsubstituted, linear or branched $C_1$-$C_{24}$ alkyl, substituted or unsubstituted $C_6$-$C_{24}$ aryl, and OR;

$R_4$ is hydrogen; and $R_5$ is hydrogen;

R is selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, and substituted or unsubstituted $C_6$-$C_{24}$ aryl;

wherein, in case of substitution, $C_1$-$C_{24}$ alkyl and $C_2$-$C_{24}$ alkenyl are substituted with 1, 2 or 3 substituents selected from the group consisting of —O—, OH, —C(═O)—$C_1$-$C_{20}$-alkyl, —C(═O)phenyl, —C(═O)—OH, —O—C(═O)—$C_1$-$C_{20}$-alkyl, —O—C(═O)—$C_1$-$C_{20}$-alkenyl, —O—C(═O)-phenyl, and unsubstituted $C_6$-$C_{24}$ aryl;

$C_6$-$C_{24}$ aryl is substituted with 1, 2 or 3 substituents selected from the group consisting of —OH, —O—$C_1$-$C_{24}$alkyl, —O-phenyl, —O—($CH_2$-phenyl), —O—($CH_2$—$CH_2$-phenyl), $CH_3$, $C_2H$, $C_3H_7$, $C_8H_{17}$, $C_{15}H_{31}$, —C(═O)—$C_1$-$C_{24}$-alkyl, —C(═O)-phenyl, —C(═O)—O—($C_1$-$C_5$-alkyl), —C(═O)—O-phenyl, and unsubstituted $C_6$-$C_{24}$ aryl.

In another preferred embodiment, the compounds of formula (A) are selected from the group consisting of i) 2-[4-[2-hydroxy-4-(oxiran-2-ylmethoxy)phenyl]-6-(2-hydroxy-4-pentadecyl-phenyl)-1,3,5-triazin-2-yl]-5-pentadecyl-phenol;

ii) 2-[4-(2-hydroxy-4-pentadecyl-phenyl)-6-(4-phenylphenyl)-1,3,5-triazin-2-yl]-5-pentadecyl-phenol;

iii) 2-[4,6-bis(4-phenylphenyl)-1,3,5-triazin-2-yl]-5-pentadecyl-phenol;

iv) 2-[4-(2-hydroxy-4-pentadecyl-phenyl)-6-(4-methoxyphenyl)-1,3,5-triazin-2-yl]-5-pentadecyl-phenol;

v) 3-[4,6-bis(4-phenylphenyl)-1,3,5-triazin-2-yl]-5-heptyl-5,6,7,8,9,10,11,12-octahydrobenzo[10]annulen-2-ol;

vi) isooctyl 2-[4-[4,6-bis(2-hydroxy-4-pentadecyl-phenyl)-1,3,5-triazin-2-yl]phenoxy]propanoate; and vii) [3-[4-[4,6-bis(2-hydroxy-4-pentadecyl-phenyl)-1,3,5-triazin-2-yl]phenoxy]-2-hydroxypropyl] 2-methylprop-2-enoate.

In another embodiment, presently claimed invention directed to an intermediate 3-(8-hydroxypentadecyl) phenol.

In another embodiment, presently claimed invention directed to a process for the preparation of 3-(8-hydroxypentadecyl) phenol.

In another embodiment, presently claimed invention directed to a process for the preparation of 3-(8-hydroxypentadecyl) phenol, comprising the steps of:

a. reducing cardanol selectively to obtain 8-monoene cardanol; and b. epoxidizing the 8-monoene cardanol followed by reduction to obtain 3-(8-hydroxypentadecyl) phenol.

In another preferred embodiment, the selective reduction of cardanol to obtain 8-monoene cardanol conducted by using a Ruthenium complex, preferably $RuCl_3$.

In another preferred embodiment, the epoxidation of 8-monoene cardanol is performed using an epoxidizing agent, selected from the group consisting of hydrogen peroxide and peracids etc.

In another preferred embodiment, the reduction of the epoxide of the cardanol is performed using LAH, sodium borohydride, $BH_3$ etc. Preferably the peracid is m-chloroperbenzoic acid.

In an embodiment, the presently claimed invention is directed to the use of a compound of formula obtained according to the presently claimed process or a compound of formula (A) as a UV absorber.

The advantages of the process of the presently claimed invention are as follows:

i) The process is commercially viable and highly cost effective.

ii) The process uses bio-available starting materials.

iii) The process provides the final product without any colour imparting impurities.

iv) The process provides novel UV absorber compound with enhanced UV absorption and weathering properties.

In the following, there is provided a list of embodiments to further illustrate the present disclosure without intending to limit the disclosure to the specific embodiments listed below.

EMBODIMENTS

1. A process for the preparation of a compound of formula (A1), formula (A1)

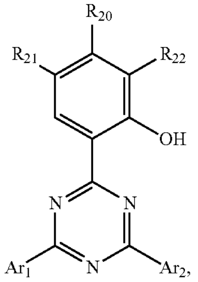

wherein $Ar_1$ and $Ar_2$ are independently of each other a moiety of the formula (B) or a moiety of the formula (J), formula (B)

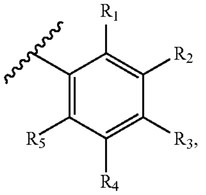

formula (J)

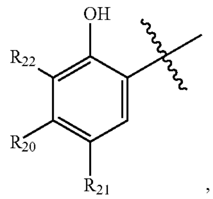

, wherein in each formulae $R_1$, $R_2$, $R_3$, $R_4$, $R_5$, $R_{20}$, $R_{21}$ and $R_{22}$ are defined as below, comprising at least the step of:

i. reacting at least one compound of formula (D) selected from the group consisting of formulae (D1), (D2) and (D3), formula (D)

formula (D1)

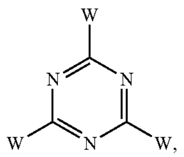

formula (D2)

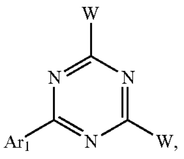

and formula (D3)

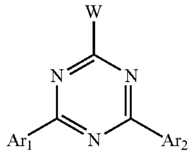

wherein W is selected from the group consisting of F, Cl, and Br; and wherein $Ar_1$ and $Ar_2$ are independently of each other a moiety of the formula (B) or a moiety of the formula (J), formula (B)

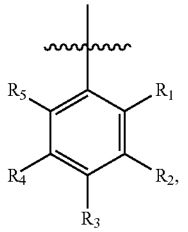

formula (J)

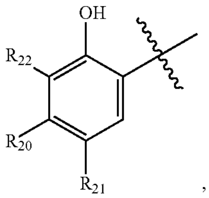

, wherein $R_1$, $R_2$, $R_3$, $R_4$ and $R_5$ are independently selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_5$-$C_{24}$ aryl, substituted or unsubstituted $C_7$-$C_{24}$ arylalkyl, —C(═O)—R, —OR, —NRR', —C(═O)—NRR', —CN, —SR, —S(═O)$_2$R, —S(═O)$_2$OH and —S(═O)$_2$OM; wherein M is an alkali metal;

or $R_1$ and $R_2$ together with the carbon atoms to which they are bonded or $R_2$ and $R_3$ together with the carbon atoms to which they are bonded or $R_3$ and $R_4$ together with the carbon atoms to which they are bonded or $R_4$ and $R_5$ together with the carbon atoms to which they are bonded form a saturated or unsaturated, unsubstituted or substituted 5- to 20-membered carbocyclic ring that optionally contains 1, 2 or 3 heteroatom(s) selected from O, N or S as ring member(s);

R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;

$R_{20}$ is selected from the group consisting of substituted or unsubstituted, linear or branched $C_{12}$-$C_{16}$ alkyl and substituted or unsubstituted, linear or branched $C_{12}$-$C_{16}$ alkenyl;

$R_{21}$ is selected from the group consisting of hydrogen, substituted or unsubstituted, linear or branched $C_{12}$-$C_{16}$ alkyl and substituted or unsubstituted, linear or branched $C_{12}$-$C_{16}$ alkenyl;

$R_{22}$ is selected from the group consisting of hydrogen and substituted or unsubstituted, linear or branched $C_1$-$C_{24}$ alkyl;

or $R_{20}$ and $R_{21}$ together with the carbon atoms to which they are bonded form a saturated or unsaturated, unsubstituted or substituted 5- to 20-membered carbocyclic ring that optionally contains 1, 2 or 3 heteroatom(s) selected from O, N or S as ring member(s);

with least one compound of formula (E), formula (E)

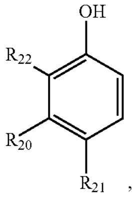

, wherein $R_{20}$, $R_{21}$ and $R_{22}$ are defined as above, in the presence of at least one acid; and ii. optionally reacting the reaction product of step i. with at least one compound of formula (G), formula (G)

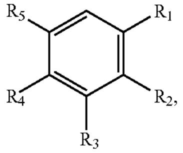

wherein $R_1$, $R_2$, $R_3$, $R_4$ and $R_5$ are defined as above, in the presence of at least one acid.

2. The process according to embodiment 1, wherein $R_1$, $R_2$, $R_3$, $R_4$ and $R_5$ are independently selected from the group consisting of hydrogen, halogen, substituted or unsubstituted, linear or branched $C_1$-$C_{24}$ alkyl, substituted or unsubstituted $C_6$-$C_{24}$ aryl, —C(═O)—R and —OR, wherein R is selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl.

3. The process according to embodiment 1 or 2, wherein $R_1$ is selected from the group consisting of hydrogen, halogen, substituted or unsubstituted, linear or branched $C_1$-$C_{24}$ alkyl, substituted or unsubstituted $C_6$-$C_{24}$ aryl, —C(═O)—R and —OR;

$R_2$ is selected from the group consisting of hydrogen, halogen, substituted or unsubstituted, linear or branched $C_1$-$C_{24}$ alkyl, substituted or unsubstituted $C_6$-$C_{24}$ aryl, substituted or unsubstituted $C_7$-$C_{24}$ arylalkyl, —C(═O)—R, —OR, —C(═O)—NRR', —CN, —S(═O)$_2$OH and —S(═O)$_2$OM; wherein M is an alkali metal;

$R_3$ is selected from the group consisting of hydrogen, halogen, substituted or unsubstituted, linear or branched $C_1$-$C_{24}$ alkyl, substituted or unsubstituted $C_5$-$C_{24}$ aryl, substituted or unsubstituted $C_7$-$C_{24}$ arylalkyl, —C(═O)R, —OR, —C(═O)—NRR', —S(═O)$_2$OH and —S(═O)$_2$OM; wherein M is an alkali metal;

$R_4$ is selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ aryl, substituted or unsubstituted $C_7$-$C_{24}$ arylalkyl, —C(═O)—R, —OR, —NRR', —C(═O)—NRR', —S(═O)$_2$OH and —S(═O)$_2$OM; wherein M is an alkali metal; and $R_5$ is selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ aryl, substituted or unsubstituted $C_7$-$C_{24}$ arylalkyl, —C(═O)—R, —OR, —NRR', —C(═O)—NRR', —S(═O)$_2$OH and —S(═O)$_2$OM; wherein M is an alkali metal;

R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_5$-$C_{24}$ aryl and substituted or unsubstituted $C_7$-$C_{24}$ arylalkyl;

wherein, in case of substitution, $C_1$-$C_{24}$ alkyl and $C_2$-$C_{24}$ alkenyl are substituted with 1, 2 or 3 substituents selected from the group consisting of —O—, OH, CN, $NH_2$, —N($C_1$-$C_5$ alkyl)$_2$, —N($C_1$-$C_5$-alkyl)(phenyl), —N($C_1$-$C_5$ alkyl)($CH_2$phenyl), —N($C_1$-$C_5$-alkyl)($CH_2$—$CH_2$-phenyl), —O—$CF_3$, —SH, —C(═O)—H, —C(═O)—$C_1$-$C_5$-alkyl, —C(═O)-phenyl, —C(═O)OH, —C(═O)—O—($C_1$-$C_{20}$-alkyl), —C(═O)—O—($C_1$-$C_{20}$-alkyl), —C(═O)—O-phenyl, —O—C(═O)($C_1$-$C_{20}$-alkyl), —O—C(═O)—($C_1$-$C_{20}$-alkenyl), —O—C(═O)-(phenyl), —C(═O)—$NH_2$, —C(═O)—NH—($C_1$-$C_5$-alkyl), —C(═O)—N($C_1$-$C_5$-alkyl)$_2$, and unsubstituted $C_6$-$C_{24}$ aryl;

$C_6$-$C_{24}$ cycloalkyl and $C_7$-$C_{24}$ cycloalkenyl are substituted with 1, 2 or 3 substituents selected from the group consisting of unsubstituted, linear or branched $C_1$-$C_{24}$ alkyl, unsubstituted, linear or branched $C_2$-$C_{24}$ alkenyl, CN, $NH_2$, —N($C_1$-$C_5$ alkyl)$_2$, —N($C_1$-$C_5$alkyl)(phenyl), —N($C_1$-$C_5$ alkyl)($CH_2$phenyl), —N($C_1$-$C_5$-alkyl)($CH_2$—$CH_2$-phenyl), —O—$CF_3$, —SH, —C(═O)—H, —C(═O)—$C_1$-$C_5$-alkyl, —C(═O)-phenyl, —C(═O)—OH, —C(═O)—O—($C_1$-$C_5$-alkyl), —C(═O)—O-phenyl, —C(═O)—$NH_2$, —C(═O)—NH—($C_1$-$C_5$-alkyl), —C(═O)—N($C_1$-$C_5$-alkyl)$_2$, and unsubstituted $C_6$-$C_{24}$ aryl and unsubstituted $C_6$-$C_{24}$ aryl;

$C_6$-$C_{24}$ aryl and $C_7$-$C_{24}$ arylalkyl are substituted with 1, 2 or 3 substituents selected from the group consisting of halogens, —CN, —S(═O)$_2$OH, —OH, —O($C_1$-$C_5$ alkyl), —O(phenyl), O($CH_2$phenyl), —O($CH_2$—$CH_2$-phenyl), S—(═O)$_2$OM, $CH_3$, $C_2H$, $C_3H_7$, $C_8H_{17}$, $C_{15}H_{31}$, $NH_2$, —O—$CF_3$, —SH, —N($C_1$-$C_5$ alkyl)$_2$, —N($C_1$-$C_5$-alkyl)(phenyl), —N($C_1$-$C_5$ alkyl)($CH_2$phenyl), —N($C_1$-$C_5$-alkyl)($CH_2$—$CH_2$-phenyl), —C(═O)—H, —C(═O)—$C_1$-$C_5$-alkyl, —C(═O)-phenyl, —C(═O)—OH, —C(═O)—O—($C_1$-$C_5$-alkyl), —C(═O)—O-phenyl, —C(═O)—$NH_2$, —C(═O)—NH—($C_1$-$C_5$-alkyl), —C(═O)—N($C_1$-$C_5$-alkyl)$_2$, and unsubstituted $C_6$-$C_{24}$ aryl.

4. The process according to embodiment 1, wherein $R_{20}$ is selected from the group consisting of linear or branched $C_{12}$-$C_{16}$ alkyl and linear or branched $C_{12}$-$C_{16}$ alkenyl; which are in each case unsubstituted or substituted with 1, 2 or 3 substituents selected from the group consisting of —OR, —S(═O)$_2$OH, —S(═O)$_2$OM, and —O—C(═O)—R, wherein M is an alkali metal;

R is selected from the group consisting of hydrogen, unsubstituted, linear or branched $C_1$-$C_{24}$ alkyl, unsubstituted, linear or branched $C_2$-$C_{24}$ alkenyl, unsubstituted $C_5$-$C_{24}$ cycloalkyl, unsubstituted $C_5$-$C_{24}$ cycloalkenyl, unsubstituted $C_6$-$C_{24}$ aryl and unsubstituted $C_7$-$C_{24}$ arylalkyl;

$R_{21}$ is selected from the group consisting of hydrogen, linear or branched $C_{12}$-$C_{16}$ alkyl and linear or branched $C_{12}$-$C_{16}$ alkenyl; which are in each case unsubstituted or substituted with 1, 2 or 3 substituents selected from the group consisting of —OR, —S(═O)$_2$OH, —S(═O)$_2$OM, and —O—C(═O)—R, moieties of formula (c1) and moieties of formula (c2), formula (c1)

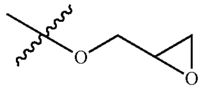

formula (c2)

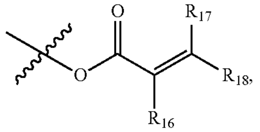

wherein M is an alkali metal;

R, $R_{16}$, $R_{17}$ and $R_{18}$ are independently selected from the group consisting of hydrogen, unsubstituted, linear or branched $C_1$-$C_{24}$ alkyl, unsubstituted, linear or branched $C_2$-$C_{24}$ alkenyl, unsubstituted $C_5$-$C_{24}$ cycloalkyl, unsubstituted $C_5$-$C_{24}$ cycloalkenyl, unsubstituted $C_6$-$C_{24}$ aryl and unsubstituted $C_7$-$C_{24}$ arylalkyl;

or $R_{20}$ and $R_{21}$ together with the carbon atoms to which they are bonded form a saturated or unsaturated, 5- to 20-membered carbocyclic ring that is unsubstituted or substituted with 1, 2 or 3 substituents selected from the group consisting of halogen, unsubstituted, linear or branched $C_1$-$C_{24}$ alkyl, unsubstituted, linear or branched $C_2$-$C_{24}$ alkenyl and unsubstituted $C_6$-$C_{24}$ aryl, and that optionally contains 1, 2 or 3 heteroatom(s) selected from O, N or S as ring member(s).

5. The process according to embodiment 1, wherein $R_{20}$ is selected from the group consisting of linear or branched $C_{14}$-$C_{16}$ alkyl and linear or branched $C_{14}$-$C_{16}$ alkenyl; which are in each case unsubstituted or substituted with 1, 2 or 3 substituents selected from the group consisting of —OR, —S—(═O)$_2$OH, —S(═O)$_2$OM, and —O—C(═O)—R, moieties of formula (c1) and moieties of formula (c2), formula (c1)

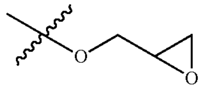

formula (c2)

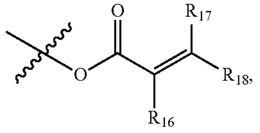

wherein M is an alkali metal;

R, $R_{16}$, $R_{17}$ and $R_{18}$ are as defined as above;

or $R_{20}$ and $R_{21}$ together with the carbon atoms to which they are bonded form a saturated or unsaturated, 5- to 20-membered carbocyclic ring.

6. The process according to embodiments 1 to 5, wherein $R_1$ is selected from the group consisting of hydrogen substituted or unsubstituted, linear or branched $C_1$-$C_{24}$ alkyl and OR;

$R_2$ is selected from the group consisting of hydrogen, substituted or unsubstituted, linear or branched $C_1$-$C_{24}$ alkyl and OR;

$R_3$ is selected from the group consisting of hydrogen, substituted or unsubstituted, linear or branched $C_1$-$C_{24}$ alkyl, substituted or unsubstituted $C_6$-$C_{24}$ aryl, and OR;

$R_4$ is hydrogen; and $R_5$ is hydrogen;

R is selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, and substituted or unsubstituted $C_6$-$C_{24}$ aryl;

wherein, in case of substitution, $C_1$-$C_{24}$ alkyl and $C_2$-$C_{24}$ alkenyl are substituted with 1, 2 or 3 substituents selected from the group consisting of —O—, OH, —C(═O)—$C_1$-$C_{20}$-alkyl, —C(═O)-phenyl, —C(═O)—OH, —O—C(═O)—($C_1$-$C_{20}$-alkyl), —O—C(═O)—($C_1$-$C_{20}$-alkenyl), —O—C(═O)-(phenyl), and unsubstituted $C_6$-$C_{24}$ aryl;

$C_6$-$C_{24}$ aryl is substituted with 1, 2 or 3 substituents selected from the group consisting of OH, O($C_1$-$C_{24}$ alkyl), O(phenyl), O($CH_2$phenyl), O($CH_2$—$CH_2$-phenyl), $CH_3$, $C_2H$, $C_3H_7$, $C_8H_{17}$, $C_{15}H_{31}$, —C(═O)—$C_1$-$C_{24}$-alkyl, —C(═O)-phenyl, —C(═O)—O—($C_1$-$C_5$-alkyl), —C(═O)—O-phenyl, and unsubstituted $C_6$-$C_{24}$ aryl.

7. The process according to embodiments 1 to 6, wherein in step i. and optional step ii. the at least one acid is selected from the group consisting of mineral acids, Lewis acids, sulfonic acids and acidic ion exchange resins.
8. The process according to embodiment 7, wherein in step i. and optional step ii. the at least one mineral acid is selected from the group consisting of sulfuric acid, hydrochloric acid, phosphoric acid, perchloric acid, nitric acid, nitrous acid, sulphurous acid, chloric acid, chlorous acid and hypochlorous acid.
9. The process according to embodiment 7, wherein in step i. and optional step ii. the at least one Lewis acid is a metal-containing compound selected from the group consisting of $AsX_3$, $GaX_3$, $BX_3$, $BX_3.(C_2H_5)_2O$, $BX_3.S(CH_3)_2$, $AlX_3$, $(C_2H)_2AlX$, $SbX_3$, $SbX_5$, $SnX_2$, $MgX_2$, $MgX_2.O(C_2H_5)_2$, $ZnX_2$, $BiX_3$, $FeX_2$, $TiX_2$, $TiX_4$, $NbX_5$, $NiX_2$, $CoX_2$, $HgX_2$, whereby X in each case denotes F, Cl, Br, $SO_3$, $CF_3$—$SO_3$, $CH_3$—$SO_3$, or I;

$BH_3$, $B(CH_3)_3$, $GaH_3$, $AlH_3$, Al(acetate)$(OH)_2$, $Al[OCH(CH_3)_2]_3$, $Al(OCH_3)_3$, $Al(OC_2H_5)_3$, $Al_2O_3$, $(CH_3)_3Al$, $Ti[OCH(CH_3)_2]_3Cl$, $Ti[OCH(CH_3)_2]_4$, methylaluminum di-(2,6-di-tertbutyl-4-methylphenoxide), methylaluminum di-(4-brom-2,6-di-tert-butylphenoxide), $LiClO_4$; Mg(acetate)$_2$, Zn(acetate)$_2$, Ni(acetate)$_2$, $Ni(NO_3)_2$, Co(acetate)$_2$, $Co(NO_3)_2$, Cu(acetate)$_2$, $Cu(NO_3)_2$, Li(acetate), Zr(acetylacetonate)$_4$, Si(acetate)$_4$, K(acetate), Na(acetate), Cs(acetate), Rb(acetate), Mn(acetate)$_2$, Fe(acetate)$_2$, Bi(acetate)$_3$, Sb(acetate)$_3$, Sr(acetate)$_2$, Sn(acetate)$_2$, Zr(acetate)$_2$, Ba(acetate)$_2$, Hg(acetate)$_2$, Ag(acetate), Tl(acetate)$_3$, Sc(fluoromethansulfonate)$_3$, Ln(fluoromethanesulfonate)$_3$, Ni(fluoromethanesulfonate)$_2$, Ni(tosylate)$_2$, Co(fluoromethanesulfonate)$_2$, Co(tosylate)$_2$, Cu(fluoromethanesulfonate)$_2$ and Cu(tosylate)$_2$.

10. The process according to embodiment 7, wherein in step i. and optional step ii. the at least one Lewis acid is selected from the group consisting of $BX_3$, $BX_3.(C_2H_5)_2O$, $BX_3.S(CH_3)_2$, $AlX_3$, $ZnX_2$, $FeX_3$ and $TiX_4$, whereby X in each case denotes F, Cl, or Br.
11. The process according to embodiment 7, wherein in step i. and optional step ii. the at least one sulfonic acid is selected from the group consisting of methanesulfonic acid, ethanesulfonic acid, 1-propanesulfonic acid, 1-butanesulfonic acid, trifluoromethanesulfonic acid, benzenesulfonic acid, p-toluenesulfonic acid, p-xylene-2-sulfonic acid, naphathalene-1-sulfonic acid and naphthalene-2-sulfonic acid.
12. The process according to embodiments 1 to 11, wherein the step i. is carried out in presence of at least one solvent.
13. The process according to embodiment 12, wherein the at least one solvent is selected from the group consisting of halogenated aliphatic hydrocarbons, halogenated aromatic hydrocarbons, carbon disulphide and polar aprotic solvents.
14. The process according to embodiment 13, wherein the halogenated aliphatic hydrocarbons are selected from the group consisting of 1,1,2,2-tetrachloroethylene, 1,1-dichloroethylene, 1,2-dichloroethylene.
15. The process according to embodiment 13, wherein the halogenated aromatic hydrocarbons are selected from the group consisting of monochlorobenzene, 1,2-dichlorobenzene, 1,3-dischlorobenzene, 1,4-dichlorobenzene, 1,3,5-trichlorobenzene.
16. The process according to embodiment 13, wherein the polar aprotic solvents are selected from the group consisting of ethers, lactones, carbonates, sulfones, N,N-dimethylformamide, N,N-dimethylacetamide, acetonitrile, dimethylsulfoxide, N-methyl-pyrrolidone and N-ethyl-pyrrolidone.
17. The process according to embodiment 16, wherein the ethers are selected from the group consisting of methyl tert-butyl ether, dioxane, diethoxy methane, dimethoxy methane, tetrahydrofuran and tetrahydropyran.
18. The process according to embodiments 1 to 17, wherein in step i. the at least one acid is present in an amount in the range of ≥20 mol.-% to ≤500 mol.-%, based on the total amount of the at least one compound of formula (D).
19. The process according to embodiments 1 to 18, wherein the step i. is carried out at a temperature in the range of ≥50° C. to ≤150° C.
20. The process according to embodiments 1 to 19, wherein step i. is conducted for a period of 30 minutes to 24 hours.
21. A compound of formula (A), formula (A)

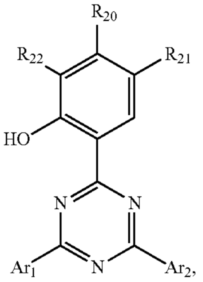

wherein $Ar_1$ and $Ar_2$ are independently of each other a moiety of the formula (B) or a moiety of the formula (J), formula (B)

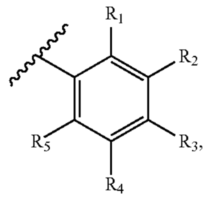

-continued formula (J)

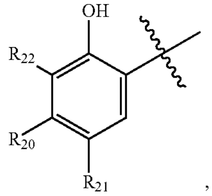

, wherein $R_1$, $R_2$, $R_3$, $R_4$ and $R_5$ are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ aryl, substituted or unsubstituted $C_7$-$C_{24}$ arylalkyl, —C(═O)—R, —OR; or $R_1$ and $R_2$ together with the carbon atoms to which they are bonded or $R_2$ and $R_3$ together with the carbon atoms to which they are bonded or $R_3$ and $R_4$ together with the carbon atoms to which they are bonded or $R_4$ and $R_5$ together with the carbon atoms to which they are bonded form a saturated or unsaturated, unsubstituted or substituted 5- to 20-membered carbocyclic ring that optionally contains 1, 2 or 3 heteroatom(s) selected from O, N or S as ring member(s); and R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;

$R_{20}$ is selected from the group consisting of substituted or unsubstituted, linear or branched $C_{12}$-$C_{16}$ alkyl, substituted or unsubstituted and linear or branched $C_{12}$-$C_{16}$ alkenyl; and $R_{21}$ is selected from the group consisting of hydrogen, substituted or unsubstituted, linear or branched $C_{12}$-$C_{16}$ alkyl and substituted or unsubstituted, linear or branched $C_{12}$-$C_{16}$ alkenyl;

$R_{22}$ is selected from the group consisting of hydrogen and substituted or unsubstituted, linear or branched $C_1$-$C_6$ alkyl; or $R_{20}$ and $R_{21}$ together with the carbon atoms to which they are bonded form a saturated or unsaturated, 5- to 20-membered carbocyclic ring that is unsubstituted or substituted with 1, 2 or 3 substituents selected from the group consisting of halogen, substituted or unsubstituted, linear or branched $C_1$-$C_{24}$ alkyl, substituted or unsubstituted, linear or branched $C_2$-$C_{24}$ alkenyl and substituted or unsubstituted $C_6$-$C_{24}$ aryl, and that optionally contains 1, 2 or 3 heteroatom(s) selected from O, N or S as ring member(s);

wherein the following compounds of formula (A) are excluded: 2-[4,6-bis(2-hydroxy-4-pentadecyl-phenyl)-1,3,5-triazin-2-yl]-5-pentadecyl-phenol and 2-(4,6-diphenyl-1,3,5-triazin-2-yl)-5-pentadecylphenol.

22. The compound according to embodiment 22, wherein $R_1$ is selected from the group consisting of hydrogen, halogen, substituted or unsubstituted, linear or branched $C_1$-$C_{24}$ alkyl, substituted or unsubstituted $C_6$-$C_{24}$ aryl, —C(═O)—R and OR;

$R_2$ is selected from the group consisting of hydrogen, halogen, substituted or unsubstituted, linear or branched $C_1$-$C_{24}$ alkyl, substituted or unsubstituted $C_6$-$C_{24}$ aryl, substituted or unsubstituted $C_7$-$C_{24}$ arylalkyl, —C(═O)—R, —OR, —S(═O)$_2$OH and —S(═O)$_2$OM; wherein M is an alkali metal;

$R_3$ is selected from the group consisting of hydrogen, halogen, substituted or unsubstituted, linear or branched $C_1$-$C_{24}$ alkyl, substituted or unsubstituted $C_6$-$C_{24}$ aryl, substituted or unsubstituted $C_7$-$C_{24}$ arylalkyl, —C(═O)—R, —OR, —S(═O)$_2$OH and —S(═O)$_2$OM; wherein M is an alkali metal;

$R_4$ is selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, —C(═O)—R, —OR, —S(═O)$_2$—OH and —S(═O)$_2$—OM; wherein M is an alkali metal; and $R_5$ is selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, —C(═O)—R, —OR, —S(═O)$_2$OH and —S(═O)$_2$OM; wherein M is an alkali metal;

R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;

wherein, in case of substitution, $C_1$-$C_{24}$ alkyl and $C_2$-$C_{24}$ alkenyl are substituted with 1, 2 or 3 substituents selected from the group consisting of —CN, $NH_2$, —N($C_1$-$C_5$ alkyl)$_2$, —N($C_1$-$C_5$-alkyl)(phenyl), —N($C_1$-$C_5$ alkyl)($CH_2$phenyl), —N($C_1$-$C_5$-alkyl)($CH_2$—$CH_2$-phenyl), —O—$CF_3$, —SH, —C(═O)—H, —C(═O)—$C_1$-$C_5$-alkyl, —C(═O)-phenyl, —C(═O)—OH, —C(═O)—O—($C_1$-$C_5$-alkyl), —C(═O)—O-phenyl, —C(═O)—$NH_2$, —C(═O)—NH—($C_1$-$C_5$-alkyl), —C(═O)—N($C_1$-$C_5$-alkyl)$_2$, and unsubstituted $C_6$-$C_{24}$ aryl;

$C_6$-$C_{24}$ cycloalkyl and $C_6$-$C_{24}$ cycloalkenyl are substituted with 1, 2 or 3 substituents selected from the group consisting of unsubstituted, linear or branched $C_1$-$C_{24}$ alkyl, unsubstituted, linear or branched $C_2$-$C_{24}$ alkenyl, CN, $NH_2$, —N($C_1$-$C_5$ alkyl)$_2$, —N($C_1$-$C_5$alkyl)(phenyl), —N($C_1$-$C_5$ alkyl)($CH_2$phenyl), —N($C_1$-$C_5$-alkyl)($CH_2$—$CH_2$-phenyl), —O—$CF_3$, —SH, —C(═O)—H, —C(═O)—$C_1$-$C_5$-alkyl, —C(═O)-phenyl, —C(═O)—OH, —C(═O)—O—($C_1$-$C_5$-alkyl), —C(═O)—O-phenyl, —C(═O)—$NH_2$, —C(═O)—NH—($C_1$-$C_5$-alkyl), —C(═O)—N($C_1$-$C_5$-alkyl)$_2$, and unsubstituted $C_6$-$C_{24}$ aryl and unsubstituted $C_6$-$C_{24}$ aryl;

$C_6$-$C_{24}$ aryl and $C_7$-$C_{24}$ arylalkyl are substituted with 1, 2 or 3 substituents selected from the group consisting of halogens, —CN, —S(═O)$_2$OH, —OH, —O($C_1$-$C_5$ alkyl), —O(phenyl), —O—($CH_2$phenyl), —O—($CH_2$—$CH_2$-phenyl), —S(═O)$_2$OM, $CH_3$, $C_2H_5$, $C_3H_7$, $C_8H_{17}$, $C_{15}H_{31}$, —$NH_2$, —O—$CF_3$, —SH, —N($C_1$-$C_5$ alkyl)$_2$, —N($C_1$-$C_5$-alkyl)(phenyl), —N($C_1$-$C_5$ alkyl)($CH_2$phenyl), —N($C_1$-$C_5$-alkyl)($CH_2$—$CH_2$-phenyl), —C(═O)—H, —C(═O)—$C_1$-$C_5$-alkyl, —C(═O)-phenyl, —C(═O)—OH, —C(═O)—O—($C_1$-$C_5$-alkyl), —C(═O)—O-phenyl, —C(═O)—$NH_2$, —C(═O)—NH—($C_1$-$C_5$-alkyl), —C(═O)—N($C_1$-$C_5$-alkyl)$_2$, and unsubstituted $C_6$-$C_{24}$ aryl;

$R_{20}$ is selected from the group consisting of linear or branched $C_{12}$-$C_{16}$ alkyl and linear or branched $C_{12}$-$C_{16}$ alkenyl; which are in each case unsubstituted or substituted with 1, 2 or 3 substituents selected from the group consisting of —OR, —S(═O)$_2$OH, —S(═O)$_2$OM, and —O—C(═O)—R, wherein M is an alkali metal;

R is selected from the group consisting of hydrogen, unsubstituted, linear or branched $C_1$-$C_{24}$ alkyl, unsubstituted, linear or branched $C_2$-$C_{24}$ alkenyl, unsubstituted $C_5$-$C_{24}$ cycloalkyl, unsubstituted $C_5$-$C_{24}$ cycloalkenyl, unsubstituted $C_6$-$C_{24}$ aryl and unsubstituted $C_7$-$C_{24}$ arylalkyl;

$R_{21}$ is selected from the group consisting of hydrogen, linear or branched $C_{12}$-$C_{16}$ alkyl and linear or branched $C_{12}$-$C_{16}$ alkenyl; which are in each case unsubstituted or substituted with 1, 2 or 3 substituents selected from the group consisting of —OR, —S(═O)$_2$OH, —S(═O)$_2$OM, and —O—C(═O)—R, moieties of formula (c1) and moieties of formula (c2), formula (c1)

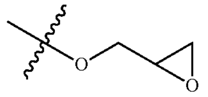

formula (c2)

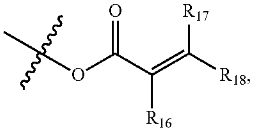

wherein M is an alkali metal;

R, $R_{16}$, $R_{17}$ and $R_{18}$ are independently selected from the group consisting of hydrogen, unsubstituted, linear or branched $C_1$-$C_{24}$ alkyl, unsubstituted, linear or branched $C_2$-$C_{24}$ alkenyl, unsubstituted $C_5$-$C_{24}$ cycloalkyl, unsubstituted $C_5$-$C_{24}$ cycloalkenyl, unsubstituted $C_6$-$C_{24}$ aryl and unsubstituted $C_7$-$C_{24}$ arylalkyl;

$R_{22}$ is selected from the group consisting of hydrogen and substituted or unsubstituted, linear or branched $C_1$-$C_4$ alkyl; or $R_{20}$ and $R_{21}$ together with the carbon atoms to which they are bonded form a saturated or unsaturated, 5- to 20-membered carbocyclic ring that is unsubstituted or substituted with 1, 2 or 3 substituents selected from the group consisting of halogen, unsubstituted, linear or branched $C_1$-$C_{24}$ alkyl, unsubstituted, linear or branched $C_2$-$C_{24}$ alkenyl and unsubstituted $C_6$-$C_{24}$ aryl, and that optionally contains 1, 2 or 3 heteroatom(s) selected from O, N or S as ring member(s).

23. The compound according to embodiments 21 and 22, wherein R1 is selected from the group consisting of hydrogen substituted or unsubstituted, linear or branched $C_1$-$C_{24}$ alkyl and OR;

$R_2$ is selected from the group consisting of hydrogen, substituted or unsubstituted, linear or branched $C_1$-$C_{24}$ alkyl and OR;

$R_3$ is selected from the group consisting of hydrogen, substituted or unsubstituted, linear or branched $C_1$-$C_{24}$ alkyl, substituted or unsubstituted $C_6$-$C_{24}$ aryl, and OR;

$R_4$ is hydrogen; and $R_5$ is hydrogen;

R is selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, and substituted or unsubstituted $C_6$-$C_{24}$ aryl;

wherein, in case of substitution, $C_1$-$C_{24}$ alkyl and $C_2$-$C_{24}$ alkenyl are substituted with 1, 2 or 3 substituents selected from the group consisting of —O—, OH, —C(═O)—$C_1$-$C_{20}$-alkyl, —C(═O)-phenyl, —C(═O)—OH, —O—C(═O)—$C_1$-$C_{20}$-alkyl, —O—C(═O)—$C_1$-$C_{20}$-alkenyl, —O—C(═O)-phenyl, and unsubstituted $C_6$-$C_{24}$ aryl;

$C_6$-$C_{24}$ aryl is substituted with 1, 2 or 3 substituents selected from the group consisting of —OH, —O—$C_1$-$C_{24}$ alkyl, —O-phenyl, —O—($CH_2$-phenyl), —O—($CH_2$—$CH_2$-phenyl), $CH_3$, $C_2H$, $C_3H_7$, $C_8H_{17}$, $C_{15}H_{31}$, —C(═O)—$C_1$-$C_{24}$-alkyl, —C(═O)-phenyl, —C(═O)—O—($C_1$-$C_5$-alkyl), —C(═O)—O-phenyl, and unsubstituted $C_6$-$C_{24}$ aryl.

24. The compound according to embodiments 21 to 23 which is selected from the group consisting of
   i) 1,3,5-Tris-(2'-hydroxy-4'-pentadecyl)phenyltriazine
   ii) 2-[4-[2-hydroxy-4-(oxiran-2-ylmethoxy)phenyl]-6-(2-hydroxy-4-pentadecyl-phenyl)-1,3,5-triazin-2-yl]-5-pentadecyl-phenol;
   iii) 2-[4-(2-hydroxy-4-pentadecyl-phenyl)-6-(4-phenylphenyl)-1,3,5-triazin-2-yl]-5-pentadecyl-phenol;
   iv) 2-[4,6-bis(4-phenylphenyl)-1,3,5-triazin-2-yl]-5-pentadecyl-phenol;
   v) 2-[4-(2-hydroxy-4-pentadecyl-phenyl)-6-(4-methoxy-phenyl)-1,3,5-triazin-2-yl]-5-pentadecyl-phenol;
   vi) 3-[4,6-bis(4-phenylphenyl)-1,3,5-triazin-2-yl]-5-heptyl-5,6,7,8,9,10,11,12-octahydrobenzo[10]annulen-2-ol;
   vii) isooctyl 2-[4-[4,6-bis(2-hydroxy-4-pentadecyl-phenyl)-1,3,5-triazin-2-yl]phenoxy]propanoate; and
   viii) [3-[4-[4,6-bis(2-hydroxy-4-pentadecyl-phenyl)-1,3,5-triazin-2-yl]phenoxy]-2-hydroxy-propyl] 2-methylprop-2-enoate.

25. Use of the compound of formula (A1) obtained according to the process of one or more of embodiments 1 to 20 or the compound of formula (A) according to embodiments 21 to 24, as a UV absorber compound.

While the presently claimed invention has been described in terms of its specific embodiments, certain modifications and equivalents will be apparent to those skilled in the art and are intended to be included within the scope of the presently claimed invention

EXAMPLES

The presently claimed invention is illustrated in detail by non-restrictive working examples which follow. More particularly, the test methods specified hereinafter are part of the general disclosure of the application and are not restricted to the specific working examples.

Materials:

| Material | Source |
|---|---|
| cyanuric chloride | Available from Sigma Aldrich |
| aluminum chloride | Available from Sigma Aldrich |
| o-dichlorobenzene | Available from Sigma Aldrich |
| Saturated cardanol | Available from Cardolite and Sigma Aldrich |
| Cardanol | Available from Cardolite |
| mono-chlorobenzene | Available from Sigma Aldrich |
| Biphenyl | Available from Sigma Aldrich |
| Octyl α-bromopropionate isomix | Available from Sigma Aldrich |
| Bromohexane | Available from Sigma Aldrich |
| Resorcinol | Available from Sigma Aldrich |
| PMMA Plexiglas 7M | Available from Evonik Industries |

-continued

| Material | Source |
| --- | --- |
| Tinuvin ® 1600:2-[4,6-bis(4-phenylphenyl)-1,3,5-triazin-2-yl]-5-(2-ethylhexoxy)phenol | Available from BASF SE |
| Cyasorb ® UV-1164:2,4-Bis(2,4-dimethylphenyl)-6-(2-hydroxy-4-n-octyloxyphenyl)-1,3,5-triazine | Available from Solvay |

Preparation of Intermediate 6-(4-phenylphenyl)-1,3,5-triazine-2,4-diol 2-butoxy-4,6-dichloro-1,3,5-triazine (70 g 315 mmol), ODCB (350 ml) and aluminum chloride (62.9 g 473 mmol) were added in 6 equal lots from 43° C. to 55° C. to a round bottom flask under nitrogen atmosphere. The above obtained reaction mixture was stirred at 55° C. for two hours. Biphenyl (43.7 g 283 mmol) in ODCB (120 ml) was added to the reaction mixture over a period of 2 hours. The reaction mass then maintained at 55° C. for 2 hours. After the completion of the reaction crude product was isolated. The crude product was purified by crystallizations using 5 volumes of chloroform to obtain 66 g (93% pure by HPLC Area %) of the 6-(4-phenylphenyl)-1,3,5-triazine-2,4-diol. Yield 79%.

Preparation of Intermediate 2,4-dichloro-6-(4-phenylphenyl)-1,3,5-triazine

Thionyl chloride 570 ml and DMF 26 ml was charged to a round bottom flask under nitrogen. To this added 6-(4-phenylphenyl)-1,3,5-triazine-2,4-diol 17 (58 g 210 mmoles) and heated to reflux and maintained at 78° C. for 2 hours. The thionyl chloride was then distilled off and the residue was stripped with toluene. The residue after stripping was added to 200 ml acetonitrile and stirred 10 minutes and filtered to obtain 55 g of 2,4-dichloro-6-(4-phenylphenyl)-1,3,5-triazine (95% HPLC Area %) Yield 83%.

Preparation of 2,4-dichloro-6-(4-methoxyphenyl)-1,3,5-triazine

Magnesium metal (7.4 g, 29.9 mmol) and tetrahydrofuran (THF, 250 ml) was charged to a round bottom flask under nitrogen. The mixture was heated to 60° C. and slowly added 4-bromoanisole (66.38 g, 28.4 mmol) in THF (100 ml) over a period of 60 min. The mixture was refluxed for 2 hours and cooled to room temperature. The above obtained mixture was added to a solution of cyanuric chloride (50.0 g, 27.1 mmol) in THF (100 ml) which was cooled to −10° C. over a period of 45 minutes by maintaining reaction temperature below −5° C. The reaction temperature was gradually allowed to rise to room temperature and stirred overnight. The product was extracted to obtain the crude product. The crude product was crystallized using 3.5 volumes of methanol. The product was dried under reduced atmosphere to obtain 44 g of 2,4-dichloro-6-(4-methoxyphenyl)-1,3,5-triazine (99% HPLC Area %) Yield 63.6%.

Comparative Example 1. Synthesis of 1,3,5-Tris-(2'-hydroxy-4'-pentadecyl)phenyltriazine (3)

Cyanuric chloride (20 g 110 mol), aluminum chloride (43 g 330 mmol) and o-dichlorobenzene (ODCB; 300 ml) were charged to a RB flask at room temperature. The reaction mass was heated to 65° C. and stirred for one hour. The temperature was increased to 80° C. and cardanol (sat) (110 g, 360 mmol) in o-dichlorobenzene (ODCB; 110 ml) was added over a period of 1 hour. The temperature of the reaction mass was maintained at 95° C. for 3 hours. After completion of the reaction the crude product was isolated. The crude product was purified by crystallizations using four volumes of ethyl acetate:methanol (92.5:7.5) to get 34 g of 1,3,5-tris-(2'-hydroxy-4'-pentadecyl)phenyltriazine (95% purity by HPLC and NMR). Yield 31%.

Example 2. Synthesis of 2-[4-(2-hydroxy-4-pentadecyl-phenyl)-6-(4-phenylphenyl)-1,3,5-triazin-2-yl]-5-pentadecyl-phenol (6)

2,4-dichloro-6-(4-phenylphenyl)-1,3,5-triazine (80 g 265 mmol) and ODCB (1000 ml) were charged to a RB flask at room temperature. The reaction mass was heated to 43 to 55° C. and slowly added $AlCl_3$ (140 g, 1054 mmol) in 6 lots maintaining the reaction temperature. The reaction mixture obtained above was purged with HCl gas over a period of 30 minutes maintaining the temperature below 60° C. Then the reaction mixture was stirred at 80 to 85° C. for 1 hour and cardanol (sat) (178 g, 582 mmol) in ODCB (400 ml) was added over a period of 60 min. The temperature of the reaction was maintained at 90° C. for 2 hours. After completion of the reaction the crude product was isolated. The crude product was purified by column chromatography using heptane:dichloromethane (80:20) to get 40.0 g of 2-[4-(2-hydroxy-4-pentadecyl-phenyl)-6-(4-phenylphenyl)-1,3,5-triazin-2-yl]-5-pentadecyl-phenol (92% HPLC Area %) Yield 18%.

Example 3. 2-[4-(2-hydroxy-4-pentadecyl-phenyl)-6-(4-methoxy phenyl)-1,3,5-triazin-2-yl]-5-pentadecyl-phenol (11)

2,4-dichloro-6-(4-methoxyphenyl)-1,3,5-triazine (33 g 12.9 mmole) and ODCB (400 ml) were charged to a RB flask at room temperature. The reaction mass was cooled to 10° C. and slowly added $AlCl_3$ (51.74 g, 38.8 mmol) in 2 lots maintaining the reaction temperature below 15° C. The reaction mixture obtained above was purged with HCl gas over a period of 45 minutes maintaining the temperature below 15° C. Then, the reaction mixture was stirred at 15° C. for 1 hour and the temperature was raised to 40° C. Cardanol (sat) (87.14 g, 25.8 mmol) in ODCB (200 ml) was added to the above reaction mixture at 40° C. over a period of 45 min. The temperature of the reaction was maintained under 40° C. for 5 hours. After completion of the reaction the crude product was isolated. The crude product was purified by column chromatography using heptane: chloroform (70:30) to get 34.0 g of 2-[4-(2-hydroxy-4-pentadecyl-phenyl)-6-(4-methoxy phenyl)-1,3,5-triazin-2-yl]-5-pentadecyl-phenol (98% HPLC Area %) Yield 34.3%.

Example 4. Synthesis of 3-[4,6-bis(4-phenylphenyl)-1,3,5-triazin-2-yl]-5-heptyl-5,6,7,8,9,10,11,12-octahydrobenzo[10]annulen-2-ol(15)

2-chloro-4,6-bis(biphenyl)-1,3,5-triazine (30 g 71.5 mmol) and ODCB (400 ml) was charged to a RB flask at room temperature. $AlCl_3$ in 2 lots (33.3 g, 250 mmol) was added to the above mixture at room temperature and heated to 55° C. The temperature of the reaction was maintained at 55° C. for 2.5 hours and 3-(8-hydroxypentadecyl) phenol (27.2 g, 85.0 mmol) in ODCB (200 ml) was added to the reaction mixture by maintaining the temperature below 90° C. over a period of 30 minutes. The temperature of reaction mixture was increased to 110° C. and maintained for 3 h at that temperature. After completion of the reaction the crude product was isolated. The crude product was purified by column chromatography using heptane:chloroform (70:30) to get 32.0 g (80% HPLC Area %) the compound. The product was recrystallized using chloroform:acetone (1:4) to obtain 23.0 g of 3-[4,6-bis(4-phenylphenyl)-1,3,5-triazin-2-yl]-5-heptyl-5,6,7,8,9,10,11,12- octahydrobenzo[10]annulen-2-ol (92% HPLC Area %) Yield 47%.

Example 5. Synthesis of [3-[4-[4,6-bis(2-hydroxy-4-pentadecyl-phenyl)-1,3,5-triazin-2-yl]-3-hydroxy-phenoxy]-2-hydroxy-propyl] 2-methylprop-2-enoate Molecule (16)

4-[4,6-bis(2-hydroxy-4-pentadecyl-phenyl)-1,3,5-triazin-2-yl]benzene-1,3-diol (0.0378 moles, 1 eq.), TBAB (0.034 moles, 0.9 eq.) DMF (180 ml) were charged to a RB flask at room temperature. Glycidyl methacrylate (0.023 moles, 0.6 eq.) was charged to above the reaction mixture at room temperature. The mixture was heated at 85° C. for 24 hours. After completion of the reaction the crude product was isolated. The product purified to get 5.0 g of [3-[4-[4,6-bis(2-hydroxy-4-pentadecyl-phenyl)-1,3,5-triazin-2-yl]-3-hydroxy-phenoxy]-2-hydroxypropyl] 2-methylprop-2-enoate Molecule. Yield 14.15%.

Example 6. Synthesis of 2-[4,6-bis(4-phenylphenyl)-1,3,5-triazin-2-yl]-5-pentadecyl-phenol (5a)

2-chloro-4,6-bis(biphenyl)-1,3,5-triazine (30 g, 71.5 mmol), mono-chlorobenzene (MCB; 400 ml) and AlC13 (38.12 g, 286 mmol) were charged to a RB flask at room temperature and heated to 60° C. The reaction mixture thus obtained, was purged with HCl gas over a period of 90 minutes. Then the reaction mixture was stirred at 60° C. for 2.5 hours. A solution containing cardanol (28.25 g, 92.9 mmol) in MCB (100 ml) was added to the reaction mixture over a period of 30 minutes and the temperature was raised to 110° C. The reaction mixture was stirred at 110° C. for 3 hours. After completion of the reaction the crude product was isolated. The crude product obtained was reprecipitated from chloroform acetone combination to get 23.0 g of 2-[4,6-bis(4-phenylphenyl)-1,3,5-triazin-2-yl]-5-pentadecyl-phenol (96% HPLC Area %). Yield 46%.

Example 7. Synthesis of 1-ethylhexyl 2-[4-[4,6-bis(2-hydroxy-4-pentadecyl-phenyl)-1,3,5-triazin-2-yl]-3-hydroxy-phenoxy] propanoate (17)

4-[4,6-bis(2-hydroxy-4-pentadecyl-phenyl)-1,3,5-triazin-2-yl] benzene-1,3-diol (38 g 47.9 mmoles), THF (330 mL), water (40 mL), PEG 400 (46 g) and $K_2CO_3$ (7.9 g 57.5 mmoles) were charged to a RB flask at room temperature and heated to 45° C. The reaction mixture was maintained at that temperature for an hour. The iso octyl mix (15.1 g 57.5 mmoles) was added at 45° C. and the reaction was maintained for further 24 h with addition of two lots of iso octyl mix (8 g 30 mmoles) after 6 and 20 hours. After completion of the reaction the crude product was isolated. The product purified to get 34.0 g of 1-ethylhexyl 2-[4-[4,6-bis(2-hydroxy-4-pentadecyl-phenyl)-1,3,5-triazin-2-yl]-3-hydroxy-phenoxy] propanoate. Yield 72%.

Solution Cast Films:

10 g PMMA (Plexiglas 7M from Evonik Industries) and the amount of additive (see table 1) are dissolved in 40 g $CH_2Cl_2$ under stirring within 2 h at room temperature.

5-10 g of this solution is poured on a glass plate in front of a coating knife (slit 120 μm, speed 12 m/s) and spread over the glass plate with the help of the coating knife.

The glass plate is now placed under an exhaust hood and the solvent is evaporated The result is a about 30 μm film Weathering of cardanol derivatives in PMMA was performed according to DIN/ISO 4892-2 Method B Cycle 5.

TABLE 1

| Compound | 0 | 307 | 592 | 880 | 1199 | 1501 | 1798 |
|---|---|---|---|---|---|---|---|
| | % Clarity (hours) | | | | | | |
| Control | 100 | 99.7 | 99.5 | 99.3 | 99.3 | 99.3 | 98.8 |
| Comparative 0.3% Tinuvin ® 1600 | 99.4 | 99.2 | 99.0 | 98.9 | 98.9 | 98.9 | 98.9 |
| Comparative 0.3% UV-1164 | 100 | 99.7 | 99.5 | 99.2 | 99.3 | 99.2 | 99.3 |
| Comparative 0.3% of 3 | 99.8 | 99.5 | 99.1 | 99.0 | 99.1 | 99.2 | 99.2 |
| 0.3% of 5a | 100 | 99.7 | 99.4 | 99.2 | 99.3 | 99.2 | 99.1 |
| 0.3% of 6 | 99.8 | 99.5 | 99.4 | 99.2 | 99.2 | 99.2 | 99.3 |
| | % Haze (hours) | | | | | | |
| Control | 0.0 | 0.9 | 1.7 | 1.7 | 3.3 | 3.3 | 0.7 |
| Comparative 0.3% Tinuvin ® 1600 | 0.3 | 0.9 | 1.9 | 2.9 | 3.4 | 3.6 | 2.0 |
| Comparative 0.3% UV-1164 | 0.1 | 0.7 | 1.7 | 3.2 | 3.7 | 4.0 | 3.5 |
| Comparative 0.3% of 3 | 0.9 | 0.5 | 3.1 | 1.7 | 3.8 | 4.9 | 1.9 |
| 0.3% of 5a | 0.3 | 0.9 | 2.3 | 3.2 | 3.5 | 4.0 | |
| 0.3% of 6 | 0.7 | 1.1 | 3.0 | 2.8 | 2.3 | 4.0 | 4.2 |
| | % Retained UV Absorbance (Hours) | | | | | | |
| Control | 0 | 0 | 0 | 0 | 0 | 0 | 0 |
| Comparative 0.3% Tinuvin ® 1600 | 100 | 102 | 103 | 98 | 92 | 90 | 81 |
| Comparative 0.3% UV-1164 | 100 | 98 | 92 | 89 | 85 | 82 | 79 |
| Comparative 0.3% of 3 | 100 | 98 | 95 | 86 | 81 | 68 | 60 |
| 0.3% of 5a | 100 | 104 | 93 | 95 | 91 | 91 | 89 |
| 0.3% of 6 | 100 | 106 | 101 | 102 | 98 | 102 | 98 |

It is evident from the above table that the compounds claimed according to presently claimed invention display comparable or higher UV absorbance. The compounds also displayed higher UV absorbance over long period as compared to the commercially available compounds. Especially compound 6 retains 100% of UV absorbance even after 1800 hours of exposure to the weathering conditions. The compounds of the presently claimed invention also displayed better or similar clarity and reduced or similar haze over longer period of exposure to the weathering conditions.

The invention claimed is:

1. A process for the preparation of a compound of formula (A1), formula (A1)

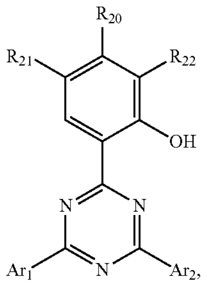

wherein $Ar_1$ and $Ar_2$ are independently of each other a moiety of the formula (B) or a moiety of the formula (J), formula (B)

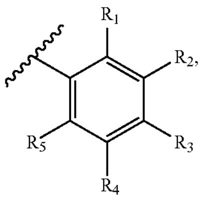

formula (J)

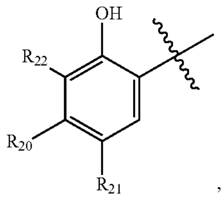

wherein in each formulae $R_1$, $R_2$, $R_3$, $R_4$, $R_5$, $R_{20}$, $R_{21}$ and $R_{22}$ are defined as below, comprising at least the step of:

i. reacting at least one compound of formula (D) selected from formulae (D1), (D2) and/or (D3), formula (D)

formula (D1)

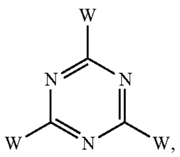

formula (D2)

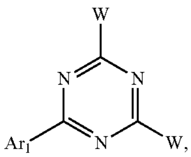

and

-continued formula (D3)

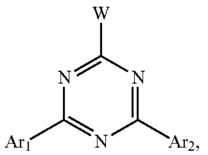

wherein W is selected from the group consisting of F, Cl, and Br; and wherein $Ar_1$ and $Ar_2$ are independently of each other a moiety of the formula (B) or a moiety of the formula (J), formula (B)

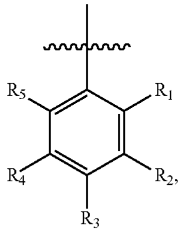

formula (J)

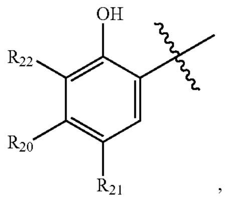

wherein $R_1$, R2, R3, $R_4$ and $R_5$ are independently selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl, substituted or unsubstituted $C_7$-$C_{24}$ arylalkyl, —C(═O)—R, —OR, —NRR', —C(═O)—NRR', —CN, —SR, —S(═O)$_2$R, —S(═O)$_2$OH and —S(═O)$_2$OM; wherein M is an alkali metal;

or $R_1$ and $R_2$ together with the carbon atoms to which they are bonded or $R_2$ and $R_3$ together with the carbon atoms to which they are bonded or $R_3$ and $R_4$ together with the carbon atoms to which they are bonded or $R_4$ and $R_5$ together with the carbon atoms to which they are bonded form a saturated or unsaturated, unsubstituted or substituted 5- to 20-membered carbocyclic ring that optionally contains 1, 2 or 3 heteroatom(s) selected from O, N or S as ring member(s); R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted C5-C24 cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;

$R_{20}$ is selected from the group consisting of substituted or unsubstituted, linear or branched $C_{12}$-$C_{16}$ alkyl and substituted or unsubstituted, linear or branched $C_{12}$-$C_{16}$ alkenyl;

$R_{21}$ is selected from the group consisting of hydrogen, substituted or unsubstituted, linear or branched $C_{12}$-$C_{16}$ alkyl and substituted or unsubstituted, linear or branched $C_{12}$-$C_{16}$ alkenyl;

$R_{22}$ is selected from the group consisting of hydrogen and substituted or unsubstituted, linear or branched $C_1$-$C_{24}$ alkyl;

Or $R_{20}$ and $R_{21}$ together with the carbon atoms to which they are bonded form a saturated or unsaturated, unsubstituted or substituted 5- to 20-membered carbocyclic ring that optionally contains 1, 2 or 3 heteroatom(s) selected from O, N or S as ring member(s);

with least one compound of formula (E), formula (E)

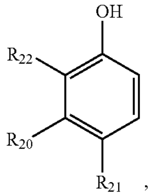

wherein $R_{20}$, $R_{21}$ and R22 are defined as above, in the presence of at least one acid; and ii. optionally reacting the reaction product of step i. with at least one compound of formula (G), formula (G)

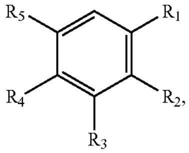

wherein $R_1$, $R_2$, $R_3$, R4 and $R_5$ are defined as above, in the presence of at least one acid.

2. The process according to claim 1, wherein $R_1$, $R_2$, $R_3$, $R_4$ and $R_5$ are independently selected from the group consisting of hydrogen, halogen, substituted or unsubstituted, linear or branched $C_1$-$C_{24}$ alkyl, substituted or unsubstituted $C_6$-$C_{24}$ aryl, —C(═O)—R and —OR, wherein R is selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl.

3. The process according to claim 1, wherein $R_1$ is selected from the group consisting of hydrogen, halogen, substituted or unsubstituted, linear or branched $C_1$-$C_{24}$ alkyl, substituted or unsubstituted $C_6$-$C_{24}$ aryl, —C(═O)—R and —OR;

$R_2$ is selected from the group consisting of hydrogen, halogen, substituted or unsubstituted, linear or branched $C_1$-$C_{24}$ alkyl, substituted or unsubstituted $C_6$-$C_{24}$ aryl, substituted or unsubstituted $C_7$-$C_{24}$ arylalkyl, —C(═O)—R, —OR, —C(═O)—NRR', —CN, —S(═O)$_2$OH and —S(═O)$_2$OM; wherein M is an alkali metal;

$R_3$ is selected from the group consisting of hydrogen, halogen, substituted or unsubstituted, linear or branched $C_1$-$C_{24}$ alkyl, substituted or unsubstituted $C_6$-$C_{24}$ aryl, substituted or unsubstituted $C_7$-$C_{24}$ arylalkyl, —C(═O)R, —OR, —C(═O)—NRR', —S(═O)$_2$OH and —S (═O)$_2$OM;

wherein M is an alkali metal;

$R_4$ is selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, —C(═O)—R, —OR, —NRR', —C(═O)—NRR', —S(═O)$_2$OH and —S(═O)$_2$OM; wherein M is an alkali metal; and $R_5$ is selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, —C(═O)—R, —OR, —NRR', —C(═O)—NRR', —S(═O)$_2$OH and —S(═O)$_2$OM; wherein M is an alkali metal;

R and R' are independently selected from the group consisting of hydrogen, substituted or unsubstituted, linear or branched $C_1$-$C_{24}$ alkyl, substituted or unsubstituted, linear or branched C2-C24 alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;

wherein, in case of substitution, $C_1$-$C_{24}$ alkyl and $C_2$-$C_{24}$ alkenyl are substituted with 1, 2 or 3 substituents selected from the group consisting of —O—, OH, CN, $NH_2$, —N($C_1$-$C_5$alkyl)$_2$,—N($C_1$-$C_5$-alkyl)(phenyl), —N($C_1$-$C_5$ alkyl)($CH_2$phenyl), —N($C_1$-$C_5$-alkyl)($CH_2$-$CH_2$-phenyl), —O—$CF_3$, —SH, —C(═O)—H, —C(═O)—$C_1$-$C_5$-alkyl, —C(═O)-phenyl, —C(═O)—OH, —C(═O)—O—($C_1$-$C_{20}$-alkyl), —C(═O)—O—($C_1$-$C_{20}$-alkyl), —C(═O)—O-phenyl, —O—C(═O)—($C_1$-$C_{20}$-alkyl), —O—C(═O)—($C_1$-$C_{20}$-alkenyl), —O—C(═O)-(phenyl), —C(═O)—$NH_2$,—C(═O)—NH—($C_1$-$C_5$-alkyl), —C(═O)—N($C_1$-$C_5$-alkyl)$_2$, and unsubstituted $C_6$-$C_{24}$ aryl;

$C_5$-$C_{24}$ cycloalkyl and $C_5$-$C_{24}$ cycloalkenyl are substituted with 1, 2 or 3 substituents selected from the group consisting of unsubstituted, linear or branched $C_1$-$C_{24}$ alkyl, unsubstituted, linear or branched $C_2$-$C_{24}$ alkenyl, CN, $NH_2$,—N($C_1$-$C_5$alkyl)$_2$,—N($C_1$-$C_5$-alkyl)(phenyl), —N($C_1$-$C_5$alkyl)($CH_2$phenyl), —N ($C_1$-$C_5$-alkyl)($CH_2$-$CH_2$-phenyl), —O—$CF_3$,—SH, —C(═O)—H, —C(═O)—$C_1$-$C_5$-alkyl, —C(═O)-phenyl, —C(═O)—OH, —C(═O)—O—($C_1$-$C_5$-alkyl), —C(═O)—O-phenyl, —C(═O)—$NH_2$,—C(═O)—NH—($C_1$-$C_5$-alkyl), —C(═O)—N($C_1$-$C_5$-alkyl)$_2$, and unsubstituted $C_6$-$C_{24}$ aryl and unsubstituted $C_6$-$C_{24}$ aryl;

$C_6$-$C_{24}$ aryl and $C_7$-$C_{24}$ arylalkyl are substituted with 1, 2 or 3 substituents selected from the group consisting of halogens, —CN, —S(═O)$_2$OH, —OH, —O($C_1$-$C_5$ alkyl), —O(phenyl), O($CH_2$phenyl), —O($CH_2$-$CH_2$-phenyl), S—(═O)$_2$OM, $CH_3$, $C_2H_5$, $C_3H_7$, $C_8H_{17}$, $C_{15}H_{31}$, $NH_2$,—O—$CF_3$,—SH, —N($C_1$-$C_5$ alkyl)$_2$,—N ($C_1$-$C_5$-alkyl)(phenyl), —N($C_1$-$C_5$alkyl)($CH_2$phenyl), —N($C_1$-$C_5$-alkyl)($CH_2$-$CH_2$phenyl), —C(═O)—H, —C(═O)—$C_1$-$C_5$-alkyl, —C(═O)-phenyl, —C(═O)—OH, —C(═O)—O—($C_1$-$C_5$-alkyl), —C(═O)—O-phenyl, —C(═O)—$NH_2$,—C(═O)—NH—($C_1$-$C_5$-alkyl), —C(═O)—N($C_1$-$C_5$-alkyl)$_2$, and unsubstituted $C_6$-$C_{24}$ aryl.

4. The process according to claim 1, wherein $R_{20}$ is selected from the group consisting of linear or branched $C_{12}$-$C_{16}$ alkyl and linear or branched $C_{12}$-$C_{16}$ alkenyl; which are in each case unsubstituted or substituted with 1, 2 or 3 substituents selected from the group consisting of —OR, —S(═O)$_2$OH, —S(═O)$_2$OM, and —O—C(═O)—R, wherein M is an alkali metal;

R is selected from the group consisting of hydrogen, unsubstituted, linear or branched $C_1$-$C_{24}$ alkyl, unsubstituted, linear or branched $C_2$-$C_{24}$ alkenyl, unsubstituted $C_5$-$C_{24}$ cycloalkyl, unsubstituted $C_5$-$C_{24}$ cycloalkenyl, unsubstituted $C_6$-$C_{24}$ aryl and unsubstituted $C_7$-$C_{24}$ arylalkyl; $R_{21}$ is selected from the group consisting of hydrogen, linear or branched $C_{12}$-$C_{16}$ alkyl and linear or branched $C_{12}$-$C_{16}$ alkenyl; which are in each case unsubstituted or substituted with 1, 2 or 3 substituents selected from the group consisting of —OR, —S(═O)$_2$OH, —S(═O)$_2$OM, and —O—C(═O)—R, moieties of formula (c1) and moieties of formula (c2), formula (c1)

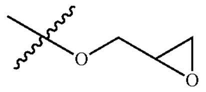

formula (c2)

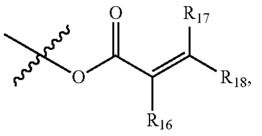

wherein M is an alkali metal;

R, $R_{16}$, $R_{17}$ and $R_{18}$ are independently selected from the group consisting of hydrogen, unsubstituted, linear or branched $C_1$-$C_{24}$ alkyl, unsubstituted, linear or branched $C_2$-$C_{24}$ alkenyl, unsubstituted $C_5$-$C_{24}$ cycloalkyl, unsubstituted $C_5$-$C_{24}$ cycloalkenyl, unsubstituted $C_6$-$C_{24}$ aryl and unsubstituted $C_7$-$C_{24}$ arylalkyl;

or $R_{20}$ and $R_{21}$ together with the carbon atoms to which they are bonded form a saturated or unsaturated, 5- to 20-membered carbocyclic ring that is unsubstituted or substituted with 1, 2 or 3 substituents selected from the group consisting of halogen, unsubstituted, linear or branched $C_1$-$C_{24}$ alkyl, unsubstituted, linear or branched $C_2$-$C_{24}$ alkenyl and unsubstituted $C_6$-C24 aryl, and that optionally contains 1, 2 or 3 heteroatom(s) selected from O, N or S as ring member(s).

5. The process according to claim 1, wherein $R_{20}$ is selected from the group consisting of linear or branched $C_{14}$-$C_{16}$ alkyl and linear or branched $C_{14}$-$C_{16}$ alkenyl; which are in each case unsubstituted or substituted with 1, 2 or 3 substituents selected from the group consisting of —OR, —S—(═O)$_2$OH, —S(═O)$_2$OM, and —O—C(═O)—R, moieties of formula (c1) and moieties of formula (c2), formula (c1)

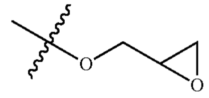

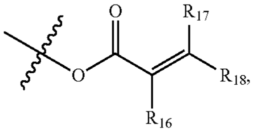

wherein M is an alkali metal;

R, $R_{16}$, $R_{17}$ and $R_{18}$ are as defined as above;

or $R_{20}$ and $R_{21}$ together with the carbon atoms to which they are bonded form a saturated or unsaturated, 5- to 20-membered carbocyclic ring.

6. The process according to claim 1, wherein R1 is selected from the group consisting of hydrogen substituted or unsubstituted, linear or branched $C_1$-$C_{24}$ alkyl and OR;

$R_2$ is selected from the group consisting of hydrogen, substituted or unsubstituted, linear or branched $C_1$-$C_{24}$ alkyl and OR;

$R_3$ is selected from the group consisting of hydrogen, substituted or unsubstituted, linear or branched $C_1$-$C_{24}$ alkyl, substituted or unsubstituted $C_6$-$C_{24}$ aryl, and OR;

$R_4$ is hydrogen; and $R_5$ is hydrogen;

R is selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, and substituted or unsubstituted $C_6$-$C_{24}$ aryl; wherein, in case of substitution, $C_1$-$C_{24}$ alkyl and $C_2$-$C_{24}$ alkenyl are substituted with 1, 2 or 3 substituents selected from the group consisting of —O—, OH, —C(═O)—$C_1$-$C_{20}$-alkyl, —C(═O)-phenyl, —C(═O)—OH, —O—C(═O)—($C_1$-$C_{20}$-alkyl), —O—C(═O)—($C_1$-$C_{20}$-alkenyl), —O—C(═O)-(phenyl), and unsubstituted $C_6$-$C_{24}$ aryl;

$C_6$-$C_{24}$ aryl is substituted with 1, 2 or 3 substituents selected from the group consisting of OH, O($C_1$-$C_{24}$ alkyl), O(phenyl), O($CH_2$phenyl), O($CH_2$-$CH_2$-phenyl), $CH_3$, $C_2H_5$, $C_3H_7$, $C_8H_{17}$, $C_{15}H_{31}$,—C(═O)—$C_1$-$C_{24}$-alkyl, —C(═O)-phenyl, —C(═O)—O—($C_1$-$C_5$-alkyl), —C(═O)—O-phenyl, and unsubstituted $C_6$-$C_{24}$ aryl.

7. The process according to claim 1, wherein in step i. and optional step ii. the at least one acid is selected from mineral acids, Lewis acids, sulfonic acids and/or acidic ion exchange resins.

8. The process according to claim 7, wherein in step i. and optional step ii. the at least one mineral acid is selected from sulfuric acid, hydrochloric acid, phosphoric acid, perchloric acid, nitric acid, nitrous acid, sulphurous acid, chloric acid, chlorous acid and/or hypochlorous acid.

9. The process according to claim 7, wherein in step i. and optional step ii. the at least one Lewis acid is a metal-containing compound selected from $AsX_3$, $GaX_3$, $BX_3$, $BX_3$.($C_2H_5$)$_2$ O $BX_3$.S($CH_3$)$_2$, $AlX_3$, ($C_2H_5$)$_2$AlX, $SbX_3$, $SbX_5$, $SnX_2$, MgX2, MgX2.O($C_2H_5$)$_2$, $ZnX_2$, $BiX_3$, $FeX_2$, $TiX_2$, $TiX_4$, $NbX_5$, $NiX_2$, $CoX_2$, $HgX_2$, whereby X in each case denotes F, Cl, Br, $SO_3$, $CF_3$-$SO_3$, $CH_3$-$SO_3$, or I;

$BH_3$, B($CH_3$)$_3$, $GaH_3$, $AlH_3$, Al(acetate)(OH)$_2$, Al[OCH($CH_3$)$_2$]$_3$, Al($OCH_3$)$_3$, Al($OC_2H_5$)$_3$, $Al_2O_3$, ($CH_3$)$_3$Al, Ti[OCH($CH_3$)$_2$]$_3$Cl, Ti[OCH($CH_3$)$_2$]$_4$, methylaluminum di-(2,6-di-tert-butyl-4-methylphenoxide), methylaluminum di-(4-brom-2,6-di-tert-butylphenoxide), $LiClO_4$; $Mg(acetate)_2$, $Zn(acetate)_2$, $Ni(acetate)_2$, $Ni(NO_3)_2$, $Co(acetate)_2$, $Co(NO_3)_2$, $Cu(acetate)_2$, $Cu(NO_3)_2$, Li(acetate), $Zr(acetylacetonate)_4$, $Si(acetate)_4$, K(acetate), Na(acetate), Cs(acetate), Rb(acetate), $Mn(acetate)_2$, $Fe(acetate)_2$, $Bi(acetate)_3$, $Sb(acetate)_3$, $Sr(acetate)_2$, $Sn(acetate)_2$, Zr $(acetate)_2$, $Ba(acetate)_2$, $Hg(acetate)_2$, Ag(acetate), $Tl(acetate)_3$, $Sc(fluoromethansulfonate)_3$, $Ln(fluoromethanesulfonate)_3$, $Ni(fluoromethanesulfonate)_2$, $Ni(tosylate)_2$, $Co(fluoromethanesulfonate)_2$, $Co(tosylate)_2$, $Cu(fluoromethanesulfonate)_2$ and/or $Cu(tosylate)_2$.

10. The process according to claim 7, wherein in step i. and optional step ii. the at least one Lewis acid is selected from $BX_3$, $BX_3.(C_2H_5)_2O$, $BX_3.S(CH_3)_2$, $AlX_3$, $ZnX_2$, $FeX_3$ and/or $TiX_4$, whereby X in each case denotes F, Cl, or Br.

11. The process according to claim 7, wherein in step i. and optional step ii. the at least one sulfonic acid is selected from methanesulfonic acid, ethanesulfonic acid, 1-propanesulfonic acid, 1-butanesulfonic acid, trifluoromethanesulfonic acid, benzenesulfonic acid, p-toluenesulfonic acid, p-xylene-2-sulfonic acid, naphathalene-1-sulfonic acid and/or naphthalene-2-sulfonic acid.

12. The process according to claim 1, wherein the step i. is carried out in presence of at least one solvent.

13. The process according to claim 12, wherein the at least one solvent is selected from halogenated aliphatic hydrocarbons, halogenated aromatic hydrocarbons, carbon disulphide and/or polar aprotic solvents.

14. The process according to claim 13, wherein the halogenated aliphatic hydrocarbons are selected from 1,1,2,2-tetrachloroethylene, 1,1-dichloroethylene, and or 1,2-dichloroethylene.

15. The process according to claim 13, wherein the halogenated aromatic hydrocarbons are selected from monochlorobenzene, 1,2-dichlorobenzene, 1,3-dischlorobenzene, 1,4-dichlorobenzene, and/or 1,3,5-trichlorobenzene.

16. The process according to claim 13, wherein the polar aprotic solvents are selected from ethers, lactones, carbonates, sulfones, N,N-dimethylformamide, N,N-dimethylacetamide, acetonitrile, dimethylsulfoxide, N-methyl-pyrrolidone and/or N-ethyl-pyrrolidone.

17. The process according to claim 16, wherein the ethers are selected from methyl tert-butyl ether, dioxane, diethoxy methane, dimethoxy methane, tetrahydrofuran and/or tetrahydropyran.

18. The process according to claim 1, wherein in step i. the at least one acid is present in an amount in the range of ≥20 mol.-% to ≤500 mol.-%, based on the total amount of the at least one compound of formula (D).

19. The process according to claim 1, wherein the step i. is carried out at a temperature in the range of ≥50° C. to ≤150° C.

20. The process according to claim 1, wherein step i. is conducted for a period of 30 minutes to 24 hours.

21. A compound of formula (A), formula (A)

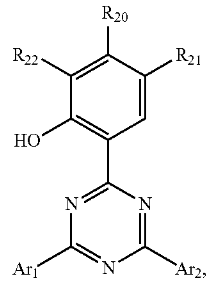

wherein $Ar_1$ and $Ar_2$ are independently of each other a moiety of the formula (B) or a moiety of the formula (J), formula (B)

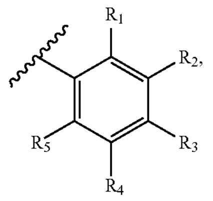

formula (J)

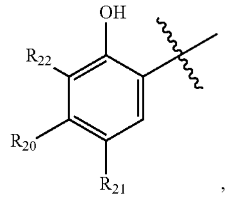

, wherein wherein $R_1$ is selected from the group consisting of hydrogen, halogen, substituted or unsubstituted, linear or branched $C_1$-$C_{24}$ alkyl, substituted or unsubstituted $C_6$-$C_{24}$ aryl, —C(═O)—R and OR;

$R_2$ is selected from the group consisting of hydrogen, halogen, substituted or unsubstituted, linear or branched $C_1$-$C_{24}$ alkyl, substituted or unsubstituted $C_6$-$C_{24}$ aryl, substituted or unsubstituted $C_7$-$C_{24}$ arylalkyl, —C(═O)—R, —OR, $—S(═O)_2OH$ and $—S(═O)_2OM$; wherein M is an alkali metal;

$R_3$ is selected from the group consisting of hydrogen, halogen, substituted or unsubstituted, linear or branched $C_1$-$C_{24}$ alkyl, substituted or unsubstituted $C_6$-$C_{24}$ aryl, substituted or unsubstituted $C_7$-$C_{24}$ arylalkyl, —C(═O)—R, $—S(═O)_2OH$ and $—S(═O)_2$ OM; wherein M is an alkali metal;

$R_4$ is selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, —C(═O)—R, —OR, $—S(═O)_2$—OH and $—S(═O)_2$—OM; wherein M is an alkali metal; and $R_5$ is selected from the group consisting of hydrogen, halogen, substituted or unsubstituted, linear or branched $C_1$-$C_{24}$ alkyl, substituted or unsubstituted, linear or branched $C_2$-$C_{24}$ alkenyl, substituted or unsubstituted $C_6$-$C_{24}$ aryl, substituted or unsubstituted $C_7$-$C_{24}$ arylalkyl, —C(═O)—R, —OR, —S(═O)$_2$OH and —S(═O)$_2$OM; wherein M is an alkali metal;

R and R' are independently selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, substituted or unsubstituted $C_5$-$C_{24}$ cycloalkenyl, substituted or unsubstituted $C_6$-$C_{24}$ aryl and substituted or unsubstituted $C_7$-$C_{24}$ arylalkyl;

wherein, in case of substitution, $C_1$-$C_{24}$ alkyl and $C_2$-$C_{24}$ alkenyl are substituted with 1, 2 or 3 substituents selected from the group consisting of —CN, $NH_2$,—N($C_1$-$C_5$ alkyl)$_2$,—N($C_1$-$C_5$-alkyl)(phenyl), —N($C_1$-$C_5$ alkyl)($CH_2$phenyl), —N($C_1$-$C_5$-alkyl)($CH_2$-$CH_2$-phenyl), —O—$CF_3$,—SH, —C(═O)—H, —C(═O)—$C_1$-$C_5$-alkyl, —C(═O)-phenyl, —C(═O)—OH, —C(═O)—O—($C_1$-$C_5$-alkyl), —C(═O)—O-phenyl, —C(═O)—$NH_2$,—C(═O)—NH—($C_1$-$C_5$-alkyl), —C(═O)—N($C_1$-$C_5$-alkyl)$_2$, and unsubstituted $C_6$-$C_{24}$ aryl;

$C_5$-$C_{24}$ cycloalkyl and $C_5$-$C_{24}$ cycloalkenyl are substituted with 1, 2 or 3 substituents selected from the group consisting of unsubstituted, linear or branched $C_1$-$C_{24}$ alkyl, unsubstituted, linear or branched $C_2$-$C_{24}$ alkenyl, CN, $NH_2$,—N($C_1$-$C_5$ alkyl)$_2$,—N($C_1$-$C_5$-alkyl)(phenyl), —N($C_1$-$C_5$alkyl)($CH_2$phenyl), —N($C_1$-$C_5$-alkyl)($CH_2$-$CH_2$-phenyl), —O—$CF_3$,—SH, —C(═O)—H, —C(═O)—$C_1$-$C_5$-alkyl, —C(═O)-phenyl, —C(═O)—OH, —C(═O)—O—($C_1$-$C_5$-alkyl), —C(═O)—O-phenyl, —C(═O)—$NH_2$,—C(═O)—NH—($C_1$-$C_5$-alkyl), —C(═O)—N($C_1$-$C_5$-alkyl)$_2$, and unsubstituted $C_6$-$C_{24}$ aryl and unsubstituted $C_6$-$C_{24}$ aryl;

$C_6$-$C_{24}$ aryl and $C_7$-$C_{24}$ arylalkyl are substituted with 1, 2 or 3 substituents selected from the group consisting of halogens, —CN, —S(═O)$_2$OH, —OH, —O($C_1$-$C_5$ alkyl), —O-(phenyl), —O—($CH_2$phenyl), —O—($CH_2$-$CH_2$-phenyl), —S(═O)$_2$OM, $CH_3$, $C_2H_5$, $C_3H_7$, $C_8H_{17}$, $C_{15}H_{31}$,—$NH_2$,—O—$CF_3$, —SH, —N($C_1$-$C_5$ alkyl)$_2$, —N($C_1$-$C_5$ alkyl, —(═O)—NH—($C_1$-$C_5$alkyl), —$C_5$-alkyl)($CH_2$-$CH_2$-phenyl), —C(═O)—H, —C(═O)—$C_1$-$C_5$-alkyl, —C(═O)-phenyl, —C(═O)—OH, —C(═O)—O—($C_1$-$C_5$-alkyl), —C(═O)—O-phenyl, —C(═O)—$NH_2$,—C(═O)—NH—($C_1$-$C_5$-alkyl), —C(═O)—N($C_1$-$C_5$-alkyl)$_2$, and unsubstituted $C_6$-$C_{24}$ aryl;

$R_{20}$ is selected from the group consisting of linear or branched $C_{12}$-$C_{16}$ alkyl and linear or branched $C_{12}$-$C_{16}$ alkenyl; which are in each case unsubstituted or substituted with 1, 2 or 3 substituents selected from the group consisting of —OR, —S(═O)$_2$OH, —S(═O)$_2$OM, and —O—C(═O)—R, wherein M is an alkali metal;

R is selected from the group consisting of hydrogen, unsubstituted, linear or branched $C_1$-$C_{24}$ alkyl, unsubstituted, linear or branched $C_2$-$C_{24}$ alkenyl, unsubstituted $C_5$-$C_{24}$ cycloalkyl, unsubstituted $C_5$-$C_{24}$ cycloalkenyl, unsubstituted $C_6$-$C_{24}$aryl and unsubstituted $C_7$-$C_{24}$ arylalkyl;

$R_{21}$ is selected from the group consisting of hydrogen, linear or branched $C_{12}$-$C_{16}$ alkyl and linear or branched $C_{12}$-$C_{16}$ alkenyl; which are in each case unsubstituted or substituted with 1, 2 or 3 substituents selected from the group consisting of —OR, —S(═O)$_2$OH, —S(═O)$_2$OM, and —O—C(═O)—R, moieties of formula (c1) and moieties of formula (c2), formula (c1)

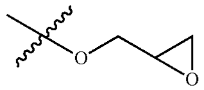

formula (c2)

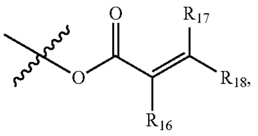

wherein M is an alkali metal;

R, $R_{16}$, $R_{17}$ and $R_{18}$ are independently selected from the group consisting of hydrogen, unsubstituted, linear or branched $C_1$-$C_{24}$ alkyl, unsubstituted, linear or branched $C_2$-$C_{24}$ alkenyl, unsubstituted $C_5$-$C_{24}$ cycloalkyl, unsubstituted $C_5$-$C_{24}$ cycloalkenyl, unsubstituted $C_6$-C24 aryl and unsubstituted $C_7$-$C_{24}$ arylalkyl;

$R_{22}$ is selected from the group consisting of hydrogen and substituted or unsubstituted, linear or branched $C_1$-$C_4$ alkyl;

or $R_{20}$ and $R_{21}$ together with the carbon atoms to which they are bonded form a saturated or unsaturated, 5- to 20-membered carbocyclic ring that is unsubstituted or substituted with 1, 2 or 3 substituents selected from the group consisting of halogen, unsubstituted, linear or branched $C_1$-$C_{24}$ alkyl, unsubstituted, linear or branched $C_2$-$C_{24}$ alkenyl and unsubstituted $C_6$-$C_{24}$ aryl, and that optionally contains 1, 2 or 3 heteroatom(s) selected from O, N or S as ring member(s), wherein the following compounds of formula (A) are excluded: 2-[4,6-bis(2-hydroxy-4-pentadecyl-phenyl)-1,3,5-triazin-2-yl]-5-pentadecyl-phenol and 2-4,6-diphenyl-1,3,5-triazin-2-yl)-5-pentadecylphenol.

22. The compound according to claim 21, wherein R1 is selected from the group consisting of hydrogen substituted or unsubstituted, linear or branched $C_1$-$C_{24}$ alkyl and OR;

$R_2$ is selected from the group consisting of hydrogen, substituted or unsubstituted, linear or branched $C_1$-$C_{24}$ alkyl and OR;

$R_3$ is selected from the group consisting of hydrogen, substituted or unsubstituted, linear or branched $C_1$-$C_{24}$ alkyl, substituted or unsubstituted $C_6$-$C_{24}$ aryl;

$R_4$ is hydrogen; and $R_5$ is hydrogen;

R is selected from the group consisting of hydrogen, substituted or unsubstituted, linear or branched $C_1$-$C_{24}$ alkyl, substituted or unsubstituted, linear or branched $C_2$-$C_{24}$ alkenyl, substituted or unsubstituted $C_5$-$C_{24}$ cycloalkyl, and substituted or unsubstituted $C_6$-$C_{24}$ aryl;

wherein, in case of substitution, $C_1$-$C_{24}$ alkyl and $C_2$-$C_{24}$ alkenyl are substituted with 1, 2 or 3 substituents selected from the group consisting of —O—, OH, —C(═O)—$C_1$-$C_{20}$-alkyl, —C(═O)-phenyl, —C(═O)—OH, —O—C(═O)—$C_1$-$C_{20}$-alkyl, —O—C(═O)—$C_1$-$C_{20}$-alkenyl, —O—C(═O)phenyl, and unsubstituted $C_6$-$C_{24}$ aryl;

$C_6$-$C_{24}$ aryl is substituted with 1, 2 or 3 substituents selected from the group consisting of —OH, —O—$C_1$-

$C_{24}$ alkyl, —O-phenyl, —O—($CH_2$-phenyl), —O—($CH_2$-$CH_2$-phenyl), $CH_3$, $C_2H_5$, $C_3H_7$, $C_8H_{17}$, $C_{15}H_{31}$, —C(═O)—$C_1$-$C_{24}$-alkyl, —C(═O)-phenyl, —C(═O)—O—($C_1$-$C_5$-alkyl), —C(═O)—O-phenyl, and unsubstituted $C_6$-$C_{24}$ aryl.

23. The compound according to claim 21, wherein the compound is:

i) 2-[4-[2-hydroxy-4-(oxiran-2-ylmethoxy)phenyl]-6-(2-hydroxy-4-pentadecyl-phenyl)-1,3,5-triazin-2-yl]-5-pentadecyl-phenol;

ii) 2-[4-(2-hydroxy-4pentadecyl-phenyl)-6-(4-phenylphenyl)-1,3,5-triazin-2-yl]-5-pentadecyl-phenol;

iii) 2-[4,6-bis(4-phenylphenyl)-1,3,5-triazin-2-yl]-5-pentadecyl-phenol;

iv) 2-[4-(2-hydroxy-4-pentadecyl-phenyl)-6-(4-methoxyphenyl)-1,3,5-triazin-2-yl]-5-pentadecyl-phenol;

v) 3-[4,6-bis(4-phenylphenyl)-1,3,5-triazin-2-yl]-5-heptyl-5,6,7,8,9,10,11,12-octahydrobenzo[10]annulen-2-ol;

vi) Isooctyl 2-[4-[4,6-bis(2-hydroxy-4-pentadecyl-phenyl)-1,3,5-triazin-2-yl]-3-hydroxy-phenoxy]propanoate; or vii) [3-[4-[4,6-bis(2-hydroxy-4-pentadecyl-phenyl)-1,3,5-triazin-2-yl]-hydroxy-phenoxy]-2-hydroxypropyl]2-methylprop-2-enoate.

* * * * *